United States Patent
Tomioka

(10) Patent No.: US 9,207,187 B2
(45) Date of Patent: Dec. 8, 2015

(54) DEVICE FOR INSPECTING RAISED FIBER STATE OF WEB MEMBERS OF SANITARY ARTICLES AND METHOD OF THE SAME

(75) Inventor: Masaharu Tomioka, Kagawa (JP)

(73) Assignee: Unicharm Corporation, Ehime (JP)

( * ) Notice: Subject to any disclaimer, the term of this patent is extended or adjusted under 35 U.S.C. 154(b) by 119 days.

(21) Appl. No.: 14/345,174

(22) PCT Filed: Sep. 6, 2012

(86) PCT No.: PCT/JP2012/072754
§ 371 (c)(1),
(2), (4) Date: Mar. 14, 2014

(87) PCT Pub. No.: WO2013/038986
PCT Pub. Date: Mar. 21, 2013

(65) Prior Publication Data
US 2014/0347467 A1 Nov. 27, 2014

(30) Foreign Application Priority Data
Sep. 15, 2011 (JP) ................................ 2011-202189

(51) Int. Cl.
*H04N 7/18* (2006.01)
*G01N 21/898* (2006.01)
(Continued)

(52) U.S. Cl.
CPC .......... *G01N 21/898* (2013.01); *G01N 21/8851* (2013.01); *G01N 21/8983* (2013.01); *G01N 2021/8444* (2013.01)

(58) Field of Classification Search
None
See application file for complete search history.

(56) References Cited

U.S. PATENT DOCUMENTS

| 6,143,393 A | 11/2000 | Abe et al. |
| 2002/0110269 A1 | 8/2002 | Floeder et al. |
| 2004/0242097 A1* | 12/2004 | Hasenoehrl ........ A44B 18/0011 442/59 |

FOREIGN PATENT DOCUMENTS

| JP | 08-14839 A | 1/1996 |
| JP | 10-251954 A | 9/1998 |
| JP | 11-235301 A | 8/1999 |

(Continued)

OTHER PUBLICATIONS

European extended Search Report from corresponding European application No. 12832542.0 dated Jun. 15, 2015 (6 pgs).

(Continued)

*Primary Examiner* — Sath V Perungavoor
*Assistant Examiner* — Dakshesh Parikh
(74) *Attorney, Agent, or Firm* — Brinks Gilson & Lione

(57) ABSTRACT

A device for inspecting a raised fiber state of a web member of a sanitary article, the web member having, on at least one face, fiber raisable parts that come off from the one face in a predetermined dispersed arrangement pattern, new exposed parts being created on the one face when the fiber raisable parts come off to be raised, wherein the inspection device includes an image capturing processing part that captures an image of the one face and creates as a planar image data, a data of a planar image of the one face, a binarization processing part that performs, when creating a binarized image based on the planar image data, a binarization process so that areas in which images of the new exposed parts in the planar image are captured, are included in an image specified by one value of two values in the binarized image, and a quality judgment processing part that performs quality judgment of the raised fiber state based on a value indicating a size of the image.

8 Claims, 11 Drawing Sheets

(51) Int. Cl.
*G01N 21/88* (2006.01)
*G01N 21/84* (2006.01)

(56) References Cited

FOREIGN PATENT DOCUMENTS

| JP | 2000-245670 | A | | 9/2000 | |
|---|---|---|---|---|---|
| JP | 2000-296084 | A | | 10/2000 | |
| JP | 2001-228142 | A | | 8/2001 | |
| JP | 2001228142 | A | * | 8/2001 | ............. G01N 33/34 |

OTHER PUBLICATIONS

International Search Report from corresponding PCT application No. PCT/JP2012/072754 dated Dec. 18, 2012 (4 pgs).
International Preliminary Report on Patentability and Written Opinion from corresponding PCT application No. PCT/JP2012/072754 dated Mar. 27, 2014 (8 pgs).

* cited by examiner

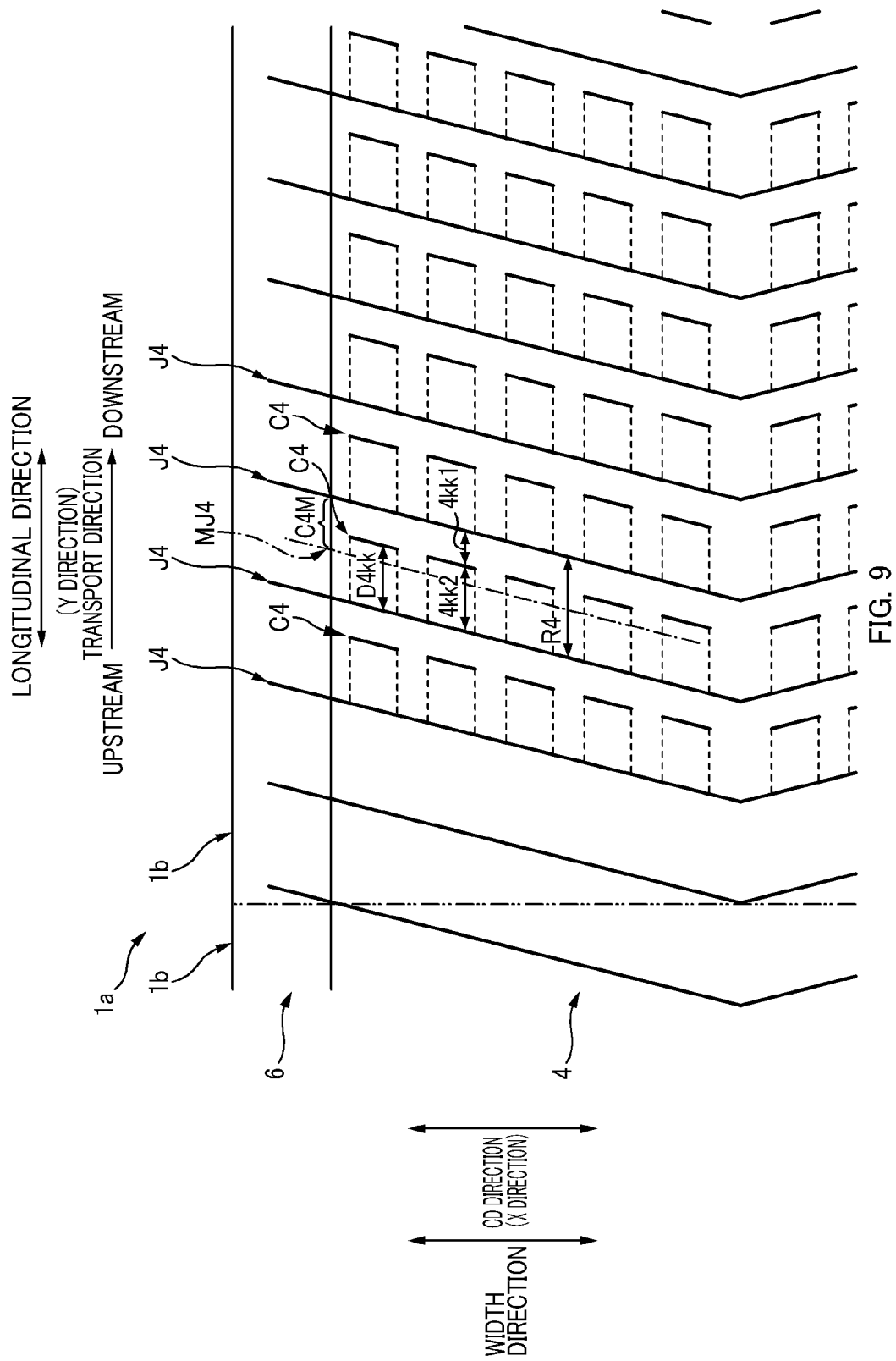

DEVICE FOR INSPECTING RAISED FIBER STATE OF WEB MEMBERS OF SANITARY ARTICLES AND METHOD OF THE SAME

RELATED APPLICATION

The present application is a 35 U.S.C. §371 national stage filing of International Patent Application No. PCT/JP2012/072754, filed Sep. 6, 2012, to which priority is claimed under 35 U.S.C. §120 and through which priority is claimed under 35 U.S.C. §119 to Japanese Priority Patent Application No. 2011-202189, filed Sep. 15, 2011.

TECHNICAL FIELD

The present invention relates to a device and a method of inspecting the raised fiber state of web members of sanitary articles such as cleaning sheets.

BACKGROUND ART

Conventionally, there has been provided cleaning sheets that are attached to a plate material which is at the tip of a handle and used for wiping the floor surface and the like. These cleaning sheets each have at least on one face thereof that becomes the main use face when used for wiping, a plurality of raisable fibrous parts that comes off from the one face and are dispersedly arranged in a predetermined pattern for improving the scraping effect of dust and the like (PTL 1).

CITATION LIST

Patent Literature

[PTL 1] Japanese Patent Application Laid-open Publication No. 2000-245670

SUMMARY OF INVENTION

Technical Problem

A pair of upper-lower brush rollers that rotate in a direction opposite the transport direction of the cleaning sheet are positioned in the vicinity of the final process in the manufacturing line of this cleaning sheet. And the cleaning sheet is passed through the roller gap between these brush rollers to thereby allow the aforementioned raisable part to come off from the one face for creating a raised fiber state and then the cleaning sheet is cut and the like into the product size for shipment.

When the brush rollers are used for a long period of time, the fibrous parts of the cleaning sheet stick to the tips of the brushes being the outer circumferential surface of the brush roller thereby reducing the raised fiber effect of the brush roller. And when such state is left as it is, cleaning sheets in insufficient raised fiber states are shipped and as a matter of course, it would be difficult for such cleaning sheets to exhibit their original scraping effect which may lead to complaints from the users.

Although inspections on the raised fiber state of the cleaning sheets after passing through the brush rollers are required, the aforementioned PTL 1 does not disclose a device or a method of inspecting the raised fiber state of the cleaning sheets. For such reasons, there had been much-awaited the inspection device and the inspection method according to the present invention.

The present invention has been made in view of the above mentioned conventional problem and an objective thereof is to provide an inspection device and an inspection method for inspecting the raised fiber states of web members of sanitary articles such as cleaning sheets.

Solution to Problem

In order to address the above problem, a primary aspect of the invention is directed to a device for inspecting a raised fiber state of a web member of a sanitary article, the web member having, on at least one face, fiber raisable parts that come off from the one face in a predetermined dispersed arrangement pattern, new exposed parts being created on the one face when the fiber raisable parts come off to be raised, wherein the inspection device includes an image capturing processing part that captures an image of the one face and creates as a planar image data, a data of a planar image of the one face, a binarization processing part that performs, when creating a binarized image based on the planar image data, a binarization process so that areas in which images of the new exposed parts in the planar image are captured, are included in an image specified by one value of two values in the binarized image, and a quality judgment processing part that performs quality judgment of the raised fiber state based on a value indicating a size of the image.

Another aspect of the invention is directed to a method for inspecting a raised fiber state of a web member of a sanitary article, the web member having, on at least one face, fiber raisable parts that come off from the one face in a predetermined dispersed arrangement pattern, new exposed parts being created on the one face when the fiber raisable parts come off to be raised, wherein the inspection method includes capturing an image of the one face and creating as a planar image data, a data of a planar image of the one face, performing, when creating a binarized image based on the planar image data, a binarization process so that areas in which images of the new exposed parts in the planar image are captured, are included in an image specified by one value of two values in the binarized image, and performing quality judgment of the raised fiber state based on a value indicating a size of the image.

Other features of the present invention will become clear from the description of the present specification with reference to the accompanying drawings.

Advantageous Effects of Invention

According to the present invention, an inspection device and an inspection method for inspecting the raised fiber state of web members of sanitary articles such as cleaning sheets can be provided.

BRIEF DESCRIPTION OF THE DRAWINGS

FIG. 4 is a schematic side view of the brush rollers 50a, 50b during the fiber raising process of the semi-manufactured product 1a.

FIG. 9 is an enlarged planar view of the semi-manufactured product 1a shown with the target forming range C4M for the cutting line C4.

DESCRIPTION OF EMBODIMENTS

Figure 1:
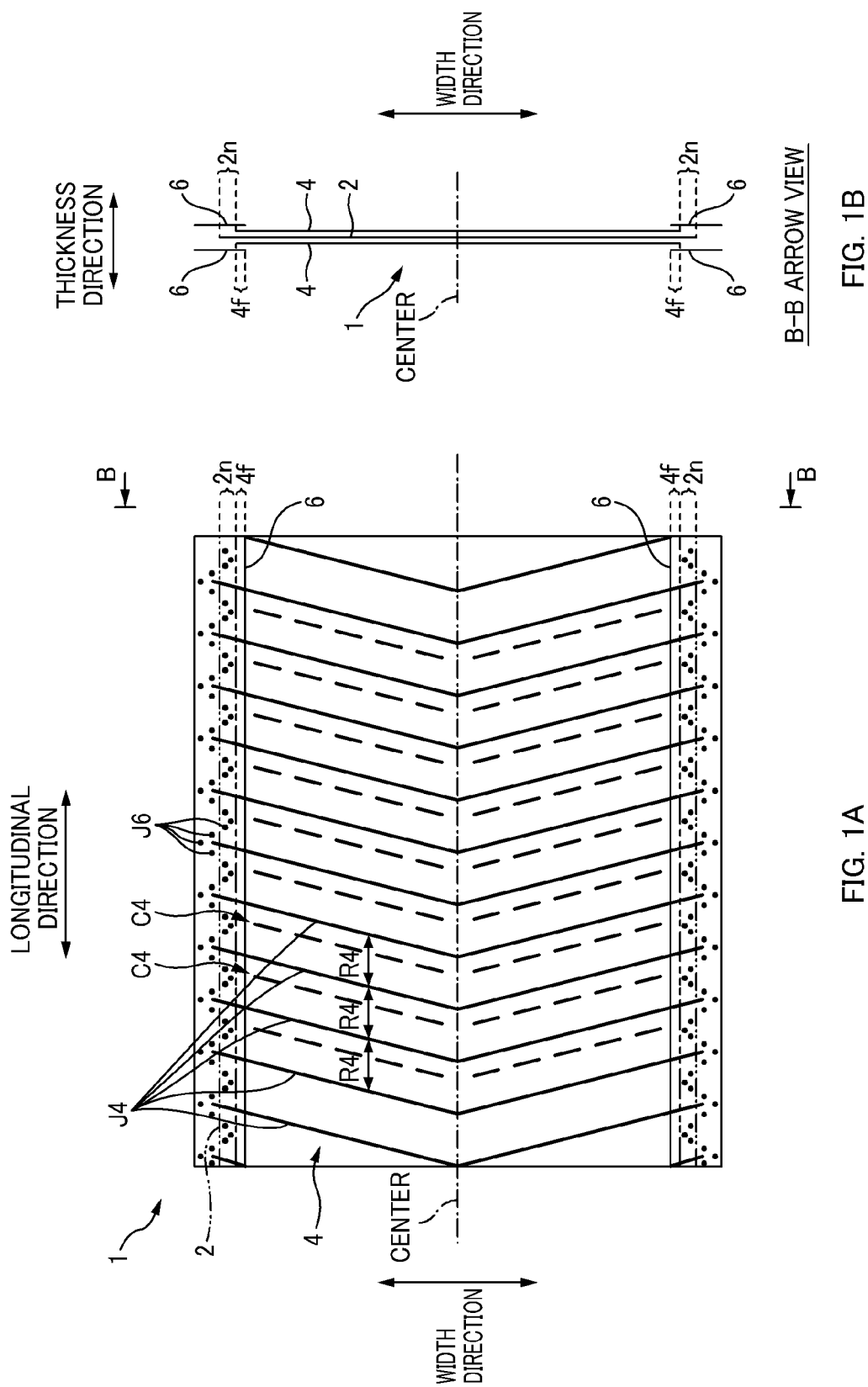
FIG. 1A is a planar view of the web product 1 in a non-raised fiber state.
FIG. 1B is a view with respect to arrows B to B in FIG. 1A.

At least the following matters will become clear from the description of the present specification with reference to the accompanying diagrammatic drawings.

A device for inspecting a raised fiber state of a web member of a sanitary article, the web member having, on at least one face, fiber raisable parts that come off from the one face in a predetermined dispersed arrangement pattern, new exposed parts being created on the one face when the fiber raisable parts come off to be raised, wherein the inspection device includes an image capturing processing part that captures an image of the one face and creates as a planar image data, a data of a planar image of the one face, a binarization processing part that performs, when creating a binarized image based on the planar image data, a binarization process so that areas in which images of the new exposed parts in the planar image are captured, are included in an image specified by one value of two values in the binarized image, and a quality judgment processing part that performs quality judgment of the raised fiber state based on a value indicating a size of the image.

According to such a device for inspecting the raised fiber states of web members of sanitary articles, a binarized image is created by a binarization process on a planar image data created on one face, and the image that is specified by one of the values of the two values in the binarized image includes an area where an image of a new exposed part in the planar image is captured. And the size of this image directly indicates the size of the new exposed part and this new exposed part is created by the raisable fiber part coming off from one face of the web member when being raised. Therefore, the size of this image can be indirectly recognized to be indicating the size of the area that is in a raised fiber state on the one face of the web member. Accordingly, the raised fiber state of the web member can be inspected by performing quality judgment on the raised fiber state based on the value indicating the size of this image.

In the device for inspecting the raised fiber states of web members of sanitary articles described above, it is preferable that the web member includes a continuous web continuing along a transport direction and a fibrous member provided to cover at least one face of the continuous web, the fibrous member has a fiber direction positioned along the transport direction, a joining part that joins the continuous web and the fibrous member, is formed intermittently in the transport direction, and the fiber raisable parts are formed by cutting the fibrous member at a cutting position between the joining parts adjacent to each other in the transport direction and configuring a cut end part of the fibrous member to be standable with the joining part as a base end part, the device for inspecting the raised fiber state of the web member of the sanitary article further including a second image capturing processing part that captures an image of a face of the fibrous member side of the web member and creates a planar image data of the fibrous member as a second planar image data, a second binarization processing part that performs when creating a binarized image based on the second planar image data, a binarization process so that an area in which an image of a cutting trace made by cutting at the cutting position is captured, is included in an image specified by one value of two values in the binarized image, and a second quality judgment processing part that judges whether or not the cutting position is positioned in a target forming range with regard to the transport direction, based on the image.

According to such a device for inspecting the raised fiber states of web members of sanitary articles, the raised fiber states of the web members can be inspected in view of the length of the raisable fiber part. Details are as follows. First, an obtained binarized image includes in one of the images a captured image of the area with the cutting traces, and a quality judgment on whether or not the cutting position is positioned in the target forming range with regard to the transport direction is made based on this image. Here, the part within the fibrous member between the cutting position and the joining part becomes the raisable fiber part. Therefore, the quality judgment on the above cutting position can be said to be indirectly determining whether the length of the raisable fiber part in the transport direction is within the target or not. Thus, the raised fiber state can be inspected in view of the length of the raisable fiber part, according to the aforementioned inspection device.

In the device for inspecting the raised fiber states of web members of sanitary articles described above, it is preferable that the second image capturing processing part that captures an image of a face on the fibrous member side of the web member, before the fiber raisable parts of the fibrous member come to be in the raised fiber state, and creates the second planar image data.

According to such a device for inspecting the raised fiber states of web members of sanitary articles, the second image capturing processing part captures images of the face on the fibrous member side with the raisable fiber part of the fibrous member in a non-raised fiber state. Therefore, images of the cutting traces can be captured with the cutting traces kept from being covered by raised fiber and hereby, a clear image of cutting traces relating to binarized images of the second planar image data can be captured. As a result, the accuracy of quality judgment on the above cutting position based on the image of this cutting trace can be improved.

In the device for inspecting the raised fiber states of web members of sanitary articles described above, it is preferable that the fibrous member is transported in the transport direction integral with the continuous web in a state covering the one face of the continuous web by being layered on the one face of the continuous web at a predetermined position in the transport direction of the continuous web, the fibrous member has a width direction in a direction orthogonal to the transport direction, the device for inspecting the raised fiber state of the web member of the sanitary article further including a third image capturing processing part that captures from one face side an image of the fibrous member before being layered on the continuous web, and creates a planar image data of the fibrous member as a third planar image data, a third binarization processing part that performs when creating a binarized image based on the third planar image data, a binarization process so that an area in which an image of a part in the fibrous member having a basis weight equal to or smaller than a predetermined value is captured, is included in an image specified by one value of two values in the binarized image, and a third quality judgment processing part that judges whether or not the basis weight of the fibrous member is uniform in the width direction, based on the image.

According to such a device for inspecting the raised fiber states of web members of sanitary articles, binarization process is performed based on the third planar image data created by taking images of the fibrous member before being overlaid on the continuous web, and then judgment is made on whether the basis weight in the width direction is uniform or not based on this binarized image. In this way, this binarized image is created based on the planar image with only the image of the fibrous member captured thereby allowing to certainly include the area whose basis weight of the fibrous member is outside the target range in one of the images of the binarized images in a state without any disturbance such as capturing an image of the continuous web without the thickness direction thereof in an overlaid state. Therefore, accurate judgment on whether the basis weight of the fibrous member in the width direction is uniform or not can be made.

Further, the third quality judgment processing part performs judgment on whether or not the basis weight of the fibrous member is uniform in the width direction. And based on this judgment result, the fibrous member can be provided to a continuous web in a state having the basis weight of the fibrous member substantially uniform in the width direction such as by appropriately adjusting the distribution in the width direction of the fibrous member. Hereby, incorrect quality judgment on the raised fiber state can be effectively prevented. Such a matter is caused by, for example, including in a binarized image subject to the raised fiber state quality judgment, an area in which an image of a part with a small basis weight captured is included in the same image as that of the area in which an image of a new exposed part made by raised fiber is captured. Thus, the accuracy of quality judgment of the raised fiber state of the web member can be improved.

In the device for inspecting the raised fiber states of web members of sanitary articles described above, it is preferable that the web member is a continuous body continuing in the transport direction, both end parts, of the one side of the web member, in the width direction orthogonal to the transport direction do not have the fiber raisable parts provided and the both end parts have thinned adhering parts formed, the binarization processing part creates the binarized image as a target of the binarization process an area besides the area in which an image of the both ends among the planar image is captured.

According to such a device for inspecting the raised fiber states of web members of sanitary articles during the binarization process, a binarized image is created excluding, among the planar image, the area in which an image of both end parts are captured, in other words, the area in which an image of the adhering parts are captured. Hereby, incorrect quality judgment on the raised fiber state can be effectively prevented. Such a matter is caused by, for example, including an area in which an image of the adhering part is captured in the same image as that of the area in which an image of a new exposed part made by raised fiber is captured. And as a result, the accuracy of quality judgment on the raised fiber state of the web member can be improved.

Further, there is provided a method for inspecting a raised fiber state of a web member of a sanitary article, the web member having, on at least one face, fiber raisable parts that come off from the one face in a predetermined dispersed arrangement pattern, new exposed parts being created on the one face when the fiber raisable parts come off to be raised, wherein the inspection method includes capturing an image of the one face and creating as a planar image data, a data of a planar image of the one face, performing, when creating a binarized image based on the planar image data, a binarization process so that areas in which images of the new exposed parts in the planar image are captured, are included in an image specified by one value of two values in the binarized image, and performing quality judgment of the raised fiber state based on a value indicating a size of the image.

According to such a method for inspecting the raised fiber states of web members of sanitary articles, a binarized image is created by a binarization process on a planar image data created on one face, and the image that is specified by one of the values of the two values in the binarized image includes an area where an image of a new exposed part in the planar image is captured. And the size of this image directly indicates the size of the new exposed part and this new exposed part is created by the raisable fiber part coming off from one face of the web member when being raised. Therefore, the size of this image can be indirectly recognized to be indicating the size of the area that is in a raised fiber state on the one face of the web member. Accordingly, the raised fiber state of the web member can be inspected by performing quality judgment on the raised fiber state based on the value indicating the size of this image.

Present Embodiment

The raised fiber state inspection device 60 of the web member 1*a* according to the present embodiment is positioned in the manufacturing line 10 for web products 1 and inspects the raised fiber state of the semi-manufactured product 1*a* before being cut into web products 1. Note that, the semi-manufactured product 1*a* as the web member 1*a* is a continuous body continuing in the transport direction of the manufacturing line 10, and this semi-manufactured product 1*a* cut into units of products is the web product 1.

Figure 2:
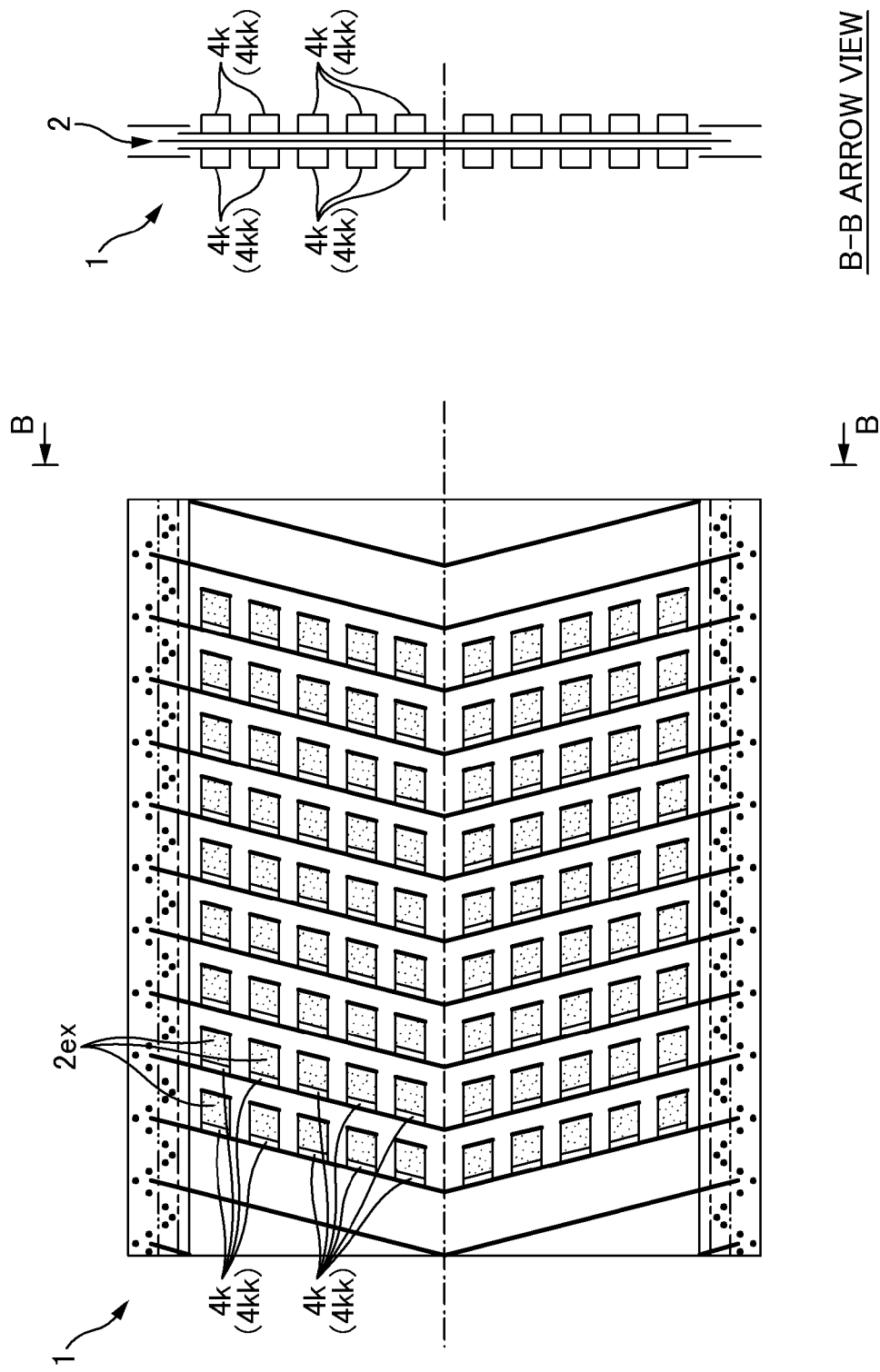
FIG. 2A is a planar view of the web product 1 in a raised fiber state.
FIG. 2B is a view with respect to arrows B to B in FIG. 2A.
Figure 3:
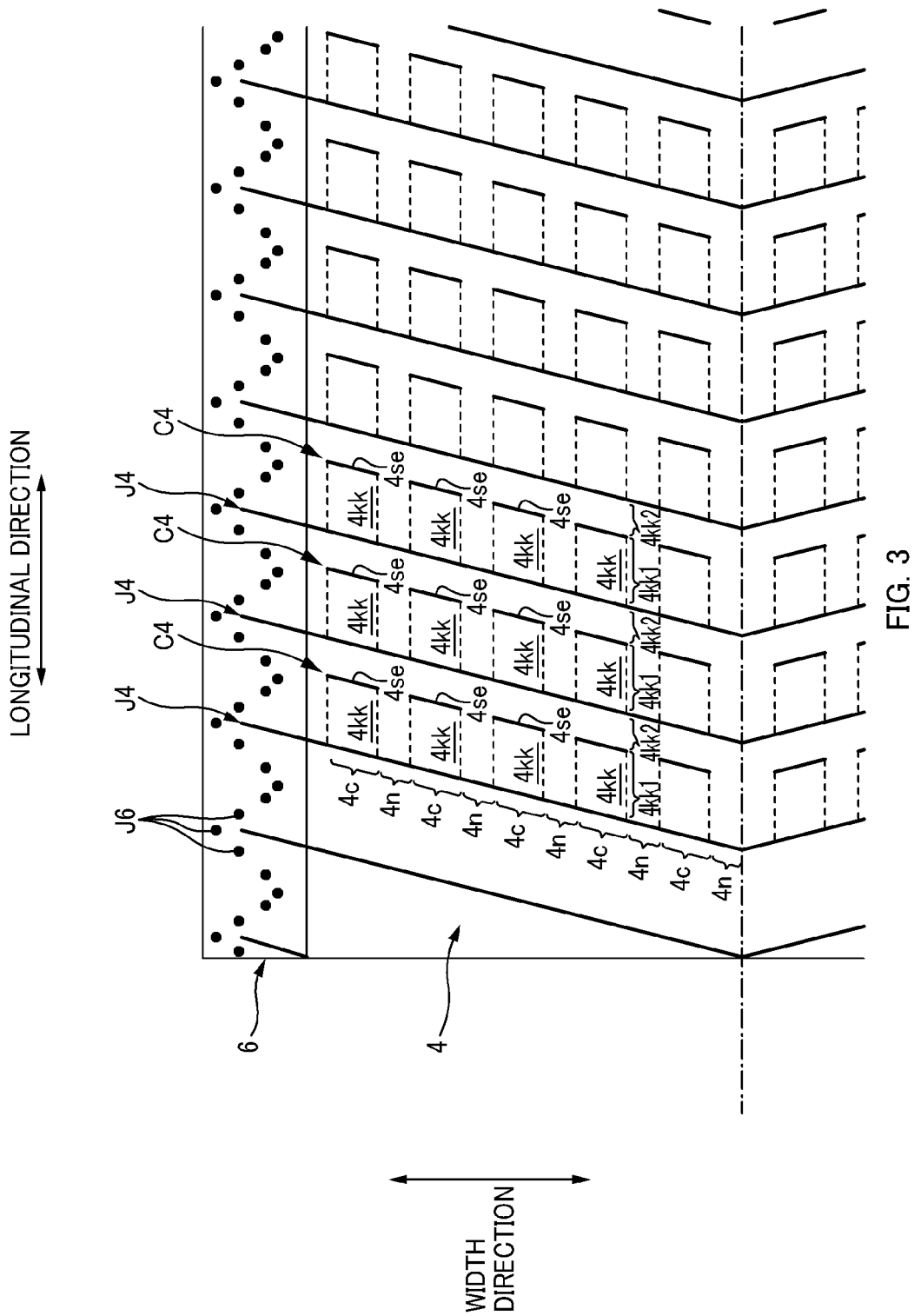
FIG. 3 is an enlarged view of the web product 1 in the non-raised fiber state.

FIG. 1A illustrates a planar view of the web product 1 in a non-raised fiber state, and FIG. 1B illustrates a view with respect to arrows B to B in FIG. 1A. FIG. 2A illustrates a planar view of the web product 1 in a raised fiber state and FIG. 2B is a view with respect to arrows B to B in FIG. 2A. FIG. 3 illustrates an enlarged view of the web product 1 in the non-raised fiber state.

This web product 1 is provided for, for example, cleaning sheets. The planar shape of the web product 1 is as shown in FIG. 1A, in a substantially rectangular shape having a longitudinal direction and a width direction. Further, as shown in FIG. 1B, the width direction is in a substantially three layered structure including the base material sheet 2, and a pair of long fibrous members 4, 4 covering both sides of the base material sheet 2 in a layer form and being fixed to the respective sides by adhesion and the like.

Note that in this example, the base material sheet 2 has a larger dimension than the long fibrous member 4 in the width direction and therefore, parts 2n, 2n that are not covered with the long fibrous member 4 exist in band shapes in predetermined widths at the two ends in the width direction. However, the base material sheet 2 may be covered along the entire width. Further in this example, each of the band shaped parts 2n, 2n that are not covered by this long fibrous member 4 are each covered by a pair of band shaped side sheets 6, 6 made of non-woven fabric from the two sides in the thickness direction. The side sheets 6, 6 are adhered and fixed to the base material sheet 2 by dotted adhering parts J6, J6 . . . in waveform arrangements, however, these side sheets 6, 6 need not be employed. Further in this example, although a part of the side sheet 6 overlaps to cover the end part 4f in the width direction of the long fibrous member 4, the end part 4f need not necessarily be covered.

Here, as shown in the enlarged view shown in FIG. 3, each of the long fibrous members 4, 4 on both sides of the web product 1 have parts 4kk (hereinafter also called fiber raisable parts 4kk) whose fibers come off the base material sheet 2 to become raisable, dispersedly arranged in a predetermined pattern. And when these fiber raisable parts 4kk, 4kk . . . are raised, a plurality of brush parts 4k are dispersedly formed in a standing manner on each face of the web product 1 as shown in FIGS. 2A and 2B, and thereby the scraping effect during cleaning is greatly improved. Note that, when forming the fiber raisable parts 4kk to the long fibrous member 4, the long fibrous member 4 need to be cut along the perforated cutting line C4. And this process of forming the fiber raisable parts 4kk into the raised fiber state is performed in the fiber raising process S50 of the manufacturing line 10 of the web product 1 which will be explained later. Description of each of the structure elements 2, 4 of the web product 1 will be given in the following.

The base material sheet 2 is a so-called shape retaining sheet for retaining the planar shape of the web product 1 and a non-woven fabric made of synthetic fiber and the like is used in this example. Note that, the base material sheet 2 is not limited to the above and may be made of film or woven cloth in some cases as long as it is a soft sheet-like member having a shape retaining function. As synthetic fiber, core-sheath conjugated fiber and single fiber and the like made of polythene or polypropylene, nylon, polyester, polyethylene terephthalate and the like can be given.

The long fibrous member 4 is a collection of numerous soft and long fibers having the fiber direction directed in the longitudinal direction of the web product 1, and is commonly called "tows". The long fibers are made of material such as polythene or polypropylene, nylon, polyester having a length of, for example, 3 to 30 mm and a fineness of, for example, 1 to 6 decitex. Further, the target value of the basis weight of the long fibrous member 4 to be layered on each face of the base material sheet 2 is each appropriately selected from a range of 20 to 100 g/m$^2$.

This base material sheet 2 and the long fibrous members 4, 4 on each side thereof, are integrally joined to one another by a plurality of joining lines J4, J4 . . . (corresponding to the joining part) formed in a predetermined pattern along substantially the entire face of the long fibrous member 4 as shown in FIG. 1A. In this example, the joining is conducted by thermal adhesion and the parts as targets of joining are pressed in the thickness direction during this thermal adhesion process. Therefore, each joining line 4J is formed in a groove form pressurized in the thickness direction. The planar shape of each joining line 4J is in a V-form each having a width extending across substantially the entire width of the web product 1. And each joining line 4J is formed to be intermittently arranged in a predetermined pitch in the longitudinal direction, with the tip part of the V-shape positioned at the center in the width direction while each of the V-shapes are arranged with their tips directed in one direction along the longitudinal direction.

Here, although there are long fibers of the long fibrous member 4 in each of the V-form areas R4 between the joining lines J4, J4 adjacent to each other in the longitudinal direction, these long fibers are fixed to the base material sheet 2 at the above mentioned pair of joining lines J4, J4. And there are perforated cutting lines C4 formed along the V-form joining line J4 in each area R4, where long fibers in each area R4 are each cut into two in the longitudinal direction along this cutting line C4. Note that, as shown in FIG. 3, this cutting line C4 in a perforated form makes the above mentioned cut intermittently in the width direction, in other words, the cut part 4c and the non-cut part 4n appear alternatively in the width direction. Then the cut part 4c has the cut end part 4se of the long fiber come in a standable state with the joining line J4 as the base end part and hereby forms the aforementioned fiber raisable part 4kk. On the other hand, the non-cut part 4n positioned adjacent to this fiber raisable part 4kk in the width direction becomes an unraised fiber unraisable part 4n. Hereby, fiber raisable parts 4kk, 4kk . . . are in a state arranged intermittently in the width direction.

Figure 4:
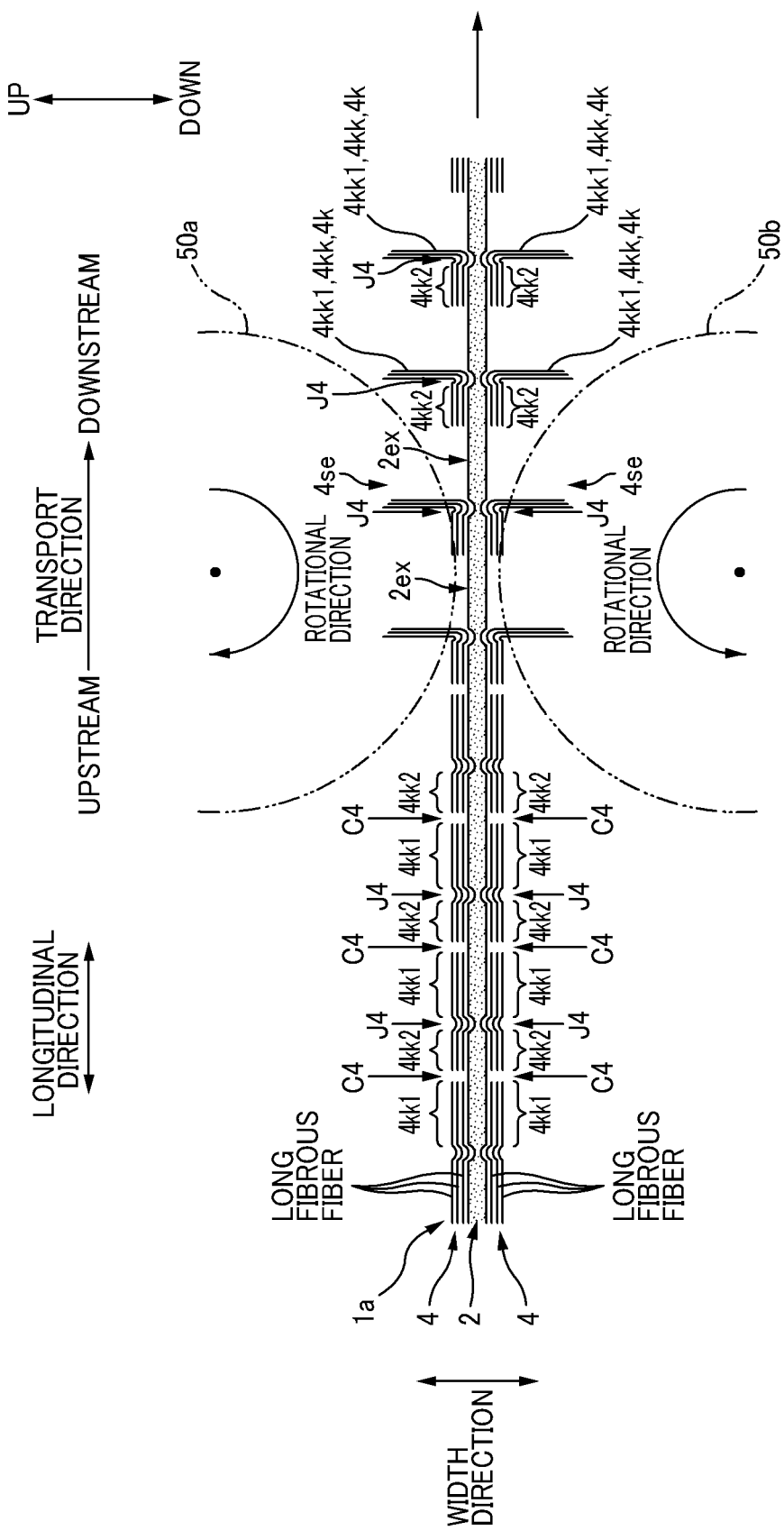

Further, the cut part 4c has two fiber raisable parts 4kk1, 4kk2 formed adjacent to each other in the longitudinal direction while sandwiching the cutting line C4, however, since the fiber raisable part 4kk2 of the two is substantially unraised, only the remaining fiber raisable part 4kk1 practically becomes the fiber raisable part 4kk. The reason for this is that the fiber raising process in the manufacturing line 10 is performed in the following manner. FIG. 4 shows a schematic side view for an explanation thereof. First, the semi-manufactured product 1a is passed through the gap between the pair of upper-lower brush rollers 50a, 50b that rotate in the direction opposite the transport direction of the semi-manufactured product 1a, and when this semi-manufactured product 1a passes through the brush rollers 50a, 50b, only the fiber raisable part 4kk1 on the upstream side in the transport direction of the pair of fiber raisable parts 4kk1, 4kk2 arranged in the longitudinal direction while sandwiching the cutting line C4 is fiber raised, and the fiber raisable part 4kk2 on the downstream side is not fiber raised. Hereby, a fiber raisable part 4kk1 and a non-raised fiber part 4kk2 also appear alternatively in the longitudinal direction. And in combination with the aforementioned fiber raisable part 4c and fiber unraisable part 4n appearing alternatively in the width direction, results in forming the fiber raisable parts 4kk, 4kk . . . intermittently in both the longitudinal direction and the width direction. In other words, as mentioned above with FIG. 3, the web product 1 is in a state having fiber raisable parts 4kk, 4kk formed dispersedly on both sides thereof.

Note that, as shown in FIG. 4, a part of the long fibers of the long fibrous member 4 comes off from the base material sheet 2 when the fiber raisable parts 4kk are fiber raised, and the cut end parts 4se are raised up in substantially the normal direction to the faces of the base material sheet 2 with the base end part as the joining line J4 of the long fibers acting as the fulcrum point. And at this time, the part 2*ex* of the base material sheet 2 that had been covered and hiding behind the long fibers being raised in the above manner, is newly exposed so to be in a state visible from the outer side. Therefore, as shown with the dotted patterns in FIG. 2A, indirect evaluation of the raised fiber state of the fiber raisable part 4*kk* is possible by observing the states of the new exposed parts 2*ex*, 2*ex* . . . of this base material sheet 2, and thus, the quality of the raised fiber state is judged by observing the states of the new exposed parts 2*ex*, 2*ex* . . . with the inspection device 60 according to the present invention. Description thereof will be given later.

Figure 5:
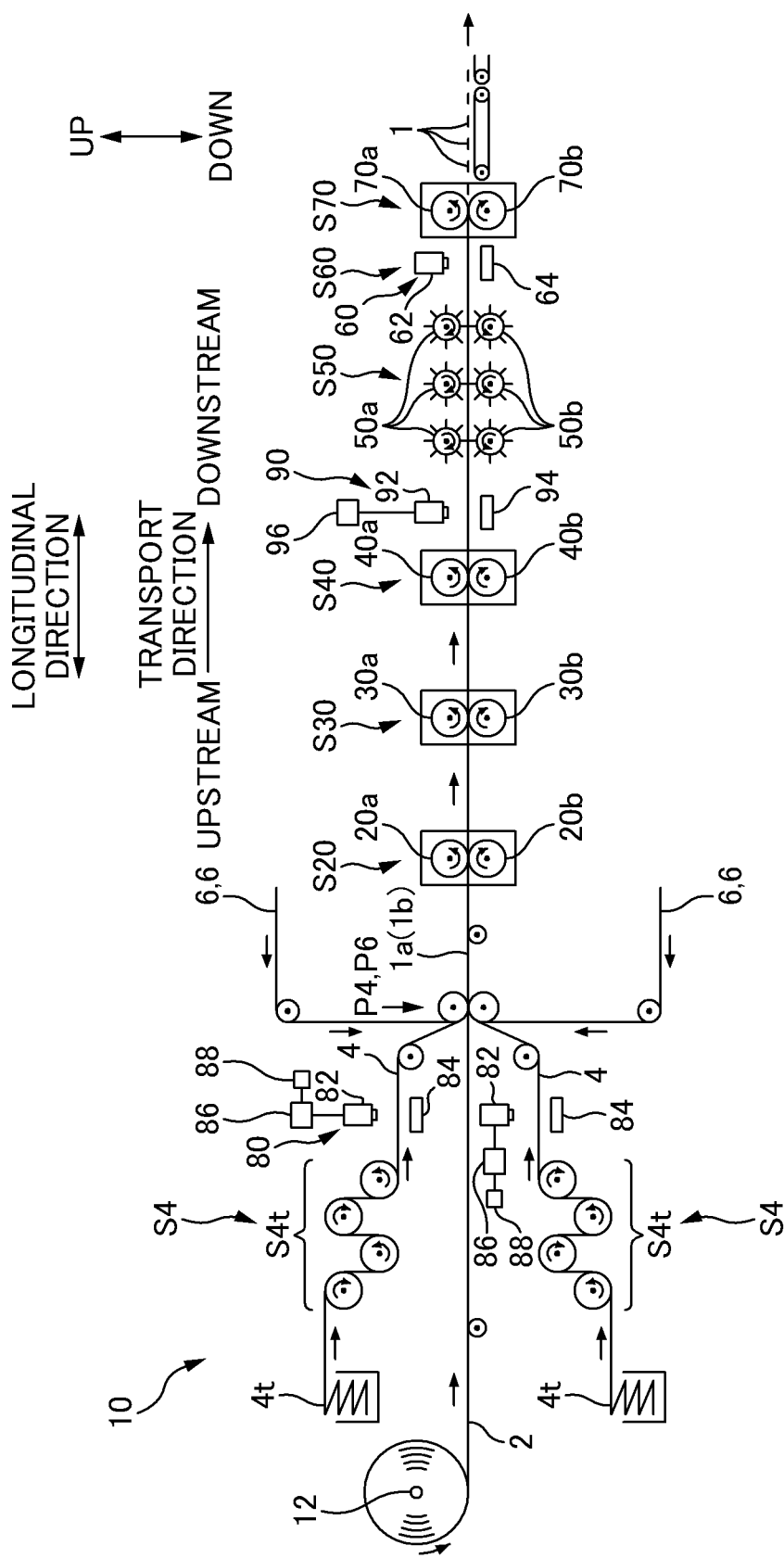
FIG. 5 is a schematic side view of the manufacturing line 10 for the web product 1.

FIG. 5 is a schematic side view of the manufacturing line 10 for the web product 1. In the manufacturing line 10, the base material sheet 2 (corresponding to the continuous web) is fed out from an appropriate reel device 12 and thereby the base material sheet 2 is continuously transported along a predetermined transport path in a continuous sheet state continuous in the transport direction. This transport path has set thereto a long fibrous member joining point P4 where the long fibrous member 4 join together, and a side sheet joining point P6 where the side sheets 6, 6, 6, 6 join together. And the long fibrous members 4, 4 (corresponding to the fibrous member) created at the long fibrous member 4 creation process S4, S4 are respectively fed and layered on and under the upper and lower surfaces being the two surfaces of the base material sheet 2, in a continuous body state continuing in the transport direction, at the long fibrous member joining point P4. Further, the side sheets 6, 6, 6, 6 created at the creation process (not shown) of the side sheet 6 are respectively fed and layered, at the two end parts in the width direction, on and under the upper and lower surfaces being the two surfaces of the base material sheet 2, in a continuous sheet state continuing in the transport direction. And thereafter, the base material sheet 2, the long fibrous members 4, 4 and the side sheets 6, 6, 6, 6 are transported along the transport path in a substantially integral manner. The transport path here, further has set thereto a main sealing process S20, a side sealing process S30, a raising fiber cutting process S40, a fiber raising process S50, a raised fiber state inspection process S60, an end cutting process S70 and the like, and the aforementioned web product 1 in a cut form is manufactured by going through these processes.

Description of the processes S20 to S70 will be given in the following, and in the following description, the continuous body that has the base material sheet 2, the long fibrous members 4, 4 and the side sheets 6, 6, 6, 6 in a substantially integral body is called the "semi-manufactured product 1*a*". By the way, the continuous direction in which this semi-manufactured product 1*a* continues is aligned with the longitudinal direction of the aforementioned web product 1. Therefore, the transport direction is also aligned with the longitudinal direction of the web product 1 and also the width direction of the semi-manufactured product 1*a* is aligned with the width direction of the web product 1. Note that this width direction is also called the "CD direction".

In the main sealing process S20, the top and bottom faces being the two faces of the base material sheet 2 each has the long fibrous members 4, 4 joined by thermal adhesion at the aforementioned V-form joining lines J4, J4 . . . . This thermal adhesion process is performed by passing the semi-manufactured product 1*a* through the roller gap between a pair of upper-lower sealing rollers 20*a*, 20*b* rotating in the transport direction. For example, the upper sealing roller 20*a* has a plurality of convex parts (not shown) with shapes corresponding to the aforementioned plurality of V-form joining lines J4, J4 . . . on its outer circumferential surface, and the lower sealing roller 20*b* has a smooth outer circumferential surface for receiving the convex parts. Therefore, when the semi-manufactured product 1*a* passes through the roller gap between this pair of rollers 20*a*, 20*b*, the parts of the semi-manufactured product 1*a* to which the convex parts abut thereagainst are selectively compressed in the thickness direction and melted to form to the semi-manufactured product 1*a* a plurality of V-form joining lines J4, J4 . . . at a predetermined pitch. Then the base material sheet 2 and the long fibrous members 4, 4 on the top and bottom faces thereof are joined integrally by these joining lines J4, J4 . . . .

In the side sealing process S30, the base material sheet 20 and the side sheets 6, 6, 6, 6 are thermally adhered and joined. The side sheets 6, 6, 6, 6 are respectively overlaid on and under the top and bottom faces being the two faces of the base material sheet 2 at both end parts in the width direction. And similar to the case of the aforementioned main sealing process S20, this thermal adhesion process is also performed by passing the semi-manufactured product 1*a* through the roller gap between a pair of upper-lower sealing rollers 30*a*, 30*b* rotating in the transport direction. For example, the upper sealing roller 30*a* has a plurality of convex parts (not shown) with shapes corresponding to the aforementioned dotted adhering parts J6, J6 . . . in waveform arrangements at the two end parts in the CD direction on its outer circumferential surface, and the bottom sealing roller 30*b* has a smooth outer circumferential surface for receiving the convex parts. Therefore, when the semi-manufactured product 1*a* passes through the roller gap between this pair of rollers 30*a*, 30*b*, the parts of the semi-manufactured product 1*a* to which the convex parts abut thereagainst are selectively compressed in the thickness direction and melted to form to the semi-manufactured product 1*a* the aforementioned dotted adhering parts J6, J6 . . . in waveform arrangements. Then the base material sheet 2 and the side sheets 6, 6, 6, 6 are joined integrally by these adhering parts J6, J6 . . . .

In the raising fiber cutting process S40, a perforated cutting line C4 is formed in each of the V-form areas R4 between the joining lines J4, J4 of the long fibrous member 4, and the aforementioned fiber raisable parts 4*kk*, 4*kk* are formed thereby. The cutting process is performed by passing the semi-manufactured product 1*a* through the roller gap between a pair of upper-lower cutter rollers 40*a*, 40*b* rotating in the transport direction. For example, the upper cutter roller 40*a* has on its outer circumferential surface cutter blades (not shown) corresponding to the aforementioned V-form perforated cutting lines C4, C4 . . . , and the lower cutter roller 40*b* has on its outer circumferential surface receiving blades (not shown) for receiving the cutter blade. Therefore, when the semi-manufactured product 1*a* passes through the roller gap between the pair of rollers 40*a*, 40*b*, the parts of the semi-manufactured product 1*a* to which the cutter blades abut thereagainst are selectively cut to form to each of the V-form areas R4, R4 between the aforementioned joining lines J4, J4 of the semi-manufactured product 1*a*, a V-form perforated cutting line C4, respectively. Then a plurality of fiber raisable parts 4*kk*, 4*kk* . . . are formed at each of the areas R4, R4 . . . with these cutting lines C4, C4 . . . .

In the fiber raising process S50, the fiber raisable parts 4*kk*, 4*kk* . . . of the long fibrous member 4 are made into a raised fiber state. This fiber raising process is performed by passing the semi-manufactured product 1*a* through the roller gap between a pair of upper-lower brush rollers 50*a*, 50*b* that rotate in the direction opposite the transport direction. For example, the upper-lower brush rollers 50*a*, 50*b* are rollers having brush members planted radially to the rotation shaft so that the tips of the brush are positioned to the outer circumferential surfaces thereof. Therefore, when the semi-manufactured product 1a passes through the gap between the pair of rollers 50a, 50b, the fiber raisable parts 4kk, 4kk . . . of the long fibrous member 4 are removed from the base material sheet 2 to be in a standing position. To be specific, with regard to the long fibrous member 4 layered on the top face of the base material sheet 2, each fiber raisable part 4kk stands up in the upright direction being substantially the normal direction to the top face of the base material sheet 2, and on the other hand, with regard to the long fibrous member 4 layered on the bottom face of the base material sheet 2, each fiber raisable part 4kk stands up in the downward direction being substantially the normal direction to the bottom face of the base material sheet 2, as shown in FIG. 4. And hereby, the semi-manufactured product 1a comes to be in a raised fiber state with the brush parts 4k vertically and dispersedly arranged on both the top and bottom faces thereof (see for example, FIGS. 2A and 2B).

The raised fiber state of the web product 1 is inspected in the raised fiber state inspection process S60. This inspection is conducted by the raised fiber state inspection device 60. And when the inspection result is of an unsatisfactory judgment, the inspection device 60 alarms the worker by, for example, setting off an unsatisfactorily raised fiber alarm. Note that description of this inspection device 60 will be given later.

In the end cutting process S70, the semi-manufactured product 1a continuing in the transport direction is cut into units of products to thereby create the web product 1 in a cut form. This cutting process performed by passing the semi-manufactured product 1a through the roller gap between a pair of upper-lower cutter rollers 70a, 70b rotating in the transport direction.

Then, the web product 1 created through the above processes is collected and the like into a predetermined number and thereafter packaged and the like in units of the collections to be shipped.

By the way, the operations of the processes S20 to S70 of the aforementioned manufacturing line 10 in the present embodiment operates by being ganged with each other using a synchronization signal. The synchronization signal is for example, when the transport amount corresponding to a single web product 1 is set as the unit transport amount, an angle of rotation signal that is generated by assigning propartally to the transport amount a value of an angle of rotation within the range of 0 to 360 degrees. In other words, when a semi-manufactured product 1a having a length corresponding to a single web product 1, a value of an angle of rotation within the range of 0 to 360 degrees is output, and this output of the value of angle of rotation within the range of 0 to 360 degrees is cyclically repeated each time this transport for a single product is made. This synchronization signal is transmitted to the amplifier of each servo motor that are the drive sources for the operations of the processes S20 to S70, and the servo motors performing position control based on this synchronization signal allows work to be performed at the target position where the work of the semi-manufactured product 1a is to be conducted.

Here, this synchronization signal is generated by a rotary type encoder provided to, for example, the sealing rollers 20a, 20b of the main sealing process. In other words, a synchronization signal is generated based on the rotational movement of the sealing roller 20a. And hereby, all the devices such as the cutter rollers 40a, 40b of the raising fiber cutting process S40 and the cutter rollers 70a, 70b of the end cutting process S70 operate to rotate in a synchronized and ganged manner with the rotational movement of the above mentioned sealing rollers 20a, 20b as the basis. Therefore, the joining line J4 formed by the sealing rollers 20a, 20b becomes the standard position of the processing with the semi-manufactured product 1a. For example, when the amount of distance between the cutting line C4 and the joining line J4 is apart from the target value, the position where the cutting line C4 is formed is adjusted with the cutter rollers 40a, 40b so that the distance becomes equal to the target value. That is, the amount of distance is made to accord with the target value by shifting the position where the cutting line C4 is formed in the transport direction with regard to the joining line J4 by changing the phase of the rotational angle value of the rotational movement of the cutter rollers 40a, 40b.

Figure 6:
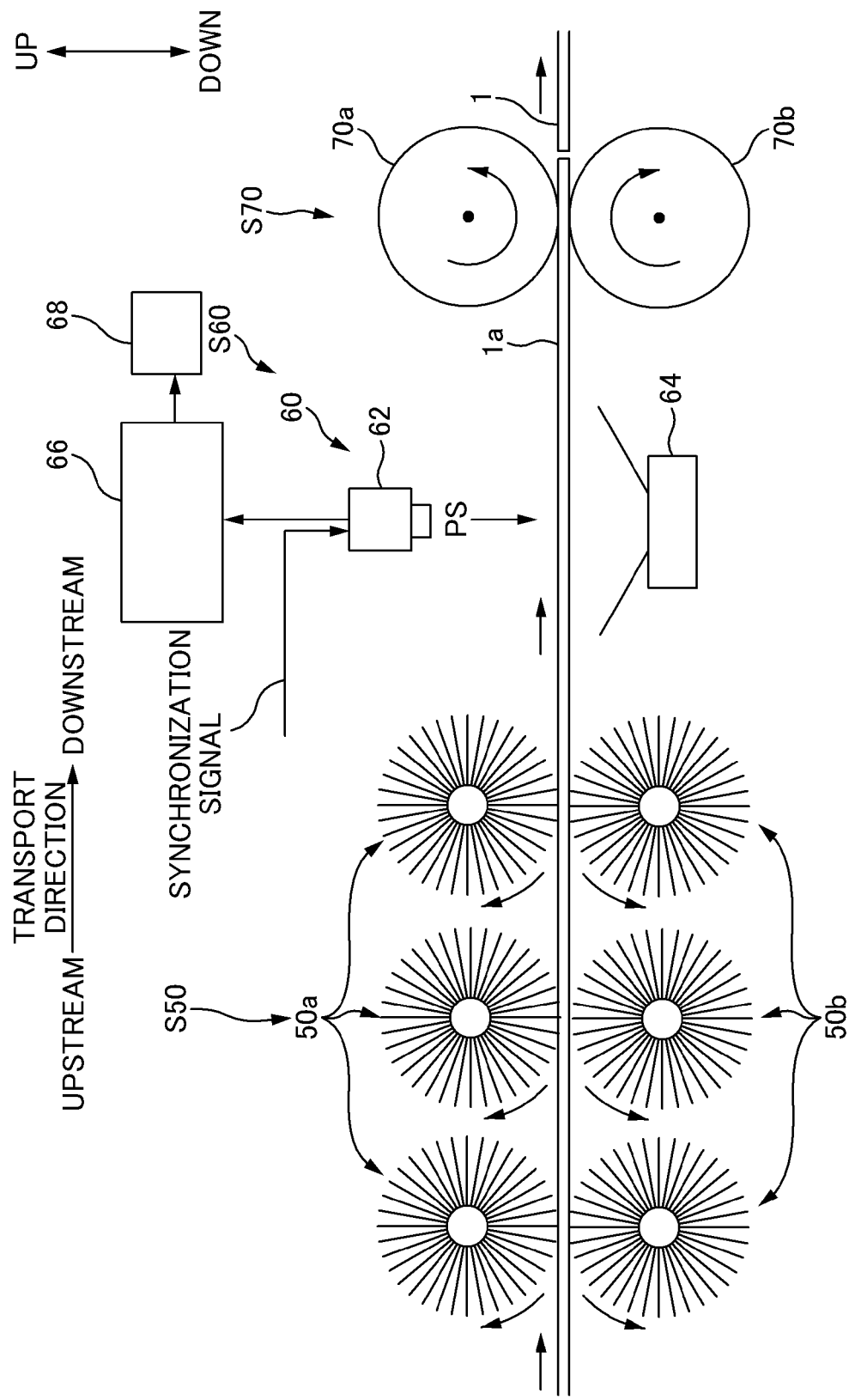
FIG. 6 is an explanatory view of the raised fiber state inspection device 60 that are positioned in the raised fiber state inspection process S60.

FIG. 6 is an explanatory view of the raised fiber state inspection device 60 positioned to the raised fiber state inspection process S60. This inspection device 60 is positioned between the fiber raising process S50 and the end cutting process S70.

This inspection device 60 inspects whether or not the fiber raisable parts 4kk, 4kk . . . of the long fibrous member 4 are raised for every unit 1b corresponding to the web product 1 in the semi-manufactured product 1a. Here, this inspection device 60 indirectly evaluates the raised fiber state of the fiber raisable part 4kk by inspecting the new exposed part 2ex of the base material sheet 2 created by raising this fiber raisable part 4kk. In other words, as shown in FIGS. 2A and 2B, the area size of the new exposed part 2ex dispersedly created along with the raising of the fiber raisable parts 4kk, 4kk . . . to the long fibrous member 4 is obtained, and is judged to be unsatisfactorily raised when this area is smaller than the predetermined quality judgment threshold. And in such case, the inspection device 60 outputs an unsatisfactorily raised fiber alarm to the alarm output part 68 of such as a monitor equipped to itself to inform a worker of the manufacturing line 10. Then the worker stops the manufacturing line 10 and removes and the like the foreign matters such as fiber stuck to the outer circumferential face of the brush rollers 50a, 50b to recover the fiber raising performance of the brush rollers 50a, 50b. Then the worker restarts manufacturing by resuming the manufacturing line 10. Note that, the unit 1b corresponding to the web product 1 of the continuous body like semi-manufactured product 1a will be called "unit semi-manufactured product 1b" in the following.

The inspection device 60 includes a camera 62 as the image capturing processing part provided at a predetermined position on the transport path of the semi-manufactured product 1a in the raised fiber state inspection process S60, a lighting member 64 positioned at a location sandwiching the transport path from above and below with the camera 62, and an image processing part 66.

The camera 62 is, for example, a CCD (charge-coupled device) camera. And the camera 62 is positioned to oppose one face of the semi-manufactured product 1a to thereby capture an image of the one face of the semi-manufactured product 1a passing by the image capturing position PS and create a planar image data. The image capturing operation is performed based on a synchronization signal and thereby captures an image of the unit semi-manufactured product 1b so that the planar center thereof substantially matches the planar center of the planar image. Here as mentioned above, the synchronization signal is, when the transport amount corresponding to a single semi-manufactured product 1b is set as the unit transport amount, an angle of rotation signal that is generated by assigning propartally to the transport amount a value of an angle of rotation within the range of 0 to 360 degrees. Therefore, if the phase of the synchronization signal corresponding to the image capturing timing when the planar center of the unit semi-manufactured product 1b and the planar center of the planar image match, as described above, is figured out as the predetermined angle of rotation value. And when the image capturing operation is set in advance to be performed with a predetermined angle of rotation value being the phase thereof, allows image capturing such that the planar center of the unit semi-manufactured product 1b matches the planar center of the planar image, as described above, for all the unit semi-manufactured products 1b that pass by the image capturing position PS thereafter.

Then, the camera 62 adjusted to such image capturing timing repeats image capturing for each unit semi-manufactured product 1b and generates data of the captured planar image as planar image data each time an image is captured. And the planar image data is transmitted to the image processing part 66 each time the data is generated. Thereafter, quality judgment on the raised fiber state of the long fibrous member 4 in the unit semi-manufactured product 1b is performed at the image processing part 66 for each unit semi-manufactured product 1b based on the planar image data. And all the web products 1 are inspected in this way. However, the present invention is not limited to the above, and for example, image capturing can be performed for every other certain number of unit semi-manufactured products 1b. And in such case, planar image data is generated for every other certain number of unit semi-manufactured products 1b so that quality judgment is also conducted for the every other certain number of unit semi-manufactured products 1b. Note that, details of the quality judgment will be described later.

The lighting member 64 is an appropriate lighting such as white LED light and fluorescent light and the type of light source is selected appropriately according to the image capturing condition of the place. Further as mentioned above, the location where the lighting member 64 is positioned is set to a location sandwiching the semi-manufactured product 1a from above and below with the camera 62 and hereby the camera 62 captures images by receiving the light of a transmitted beam transmitted through the semi-manufactured product 1a in the thickness direction.

The image processing part 66 has an appropriate computer as its main body and includes a processor and a memory. And various processes such as a binarization process is performed by the processor reading and executing various processing programs such as a binarization processing program and the like stored in the memory in advance.

At the image processing part 66, binarized images are created by performing binarization processes to transmitted planar image data. At this time, the image processing part 66 performs a binarization process so that the area in the planar image in which the new exposed part 2ex of the base material sheet 2 is captured, is included in the image specified by one of the two values (for example, 0 and 1) being "1" in the binarized image. Hereby, the area A2ex in which images of parts 2ex, 2ex, . . . of the base material sheet 2 are newly exposed by raising the fiber raisable parts 4kk, 4kk . . . are captured, is taken out as an image specified by "1" from the planar image of the unit semi-manufactured product 1b. In the following description, the image specified as "1" of the binarized image, that is, the image including the area A2ex in which the new exposed part 2ex is captured, is also called the "white image" whereas the image specified as "0" is also called the "black image".

Thereafter, the image processing part 66 performs a quality judgment on the raised fiber state by comparing the size of the area of this white image with the prescribed threshold value for quality judgment. This is called the "quality judgment process" in the following description. Additionally, the white image specified as "1" described above corresponds to the "image specified by one of the values of the two values in the binarized image", and the area size of the white image corresponds to the "value indicating the size of the image" in the claims.

Note that, similar to the aforementioned binarization processing program, the program for executing the quality judgment process is also stored in advance in the memory of the image processing part 66. And by the processor reading and executing these programs allows the image processing part 66 to function as the "binarization processing part" that executes the binarization process and the "quality judgment processing part" that executes the quality judgment process. Detailed description of the binarization process and the quality judgment process are given in the following.

Figure 7A:
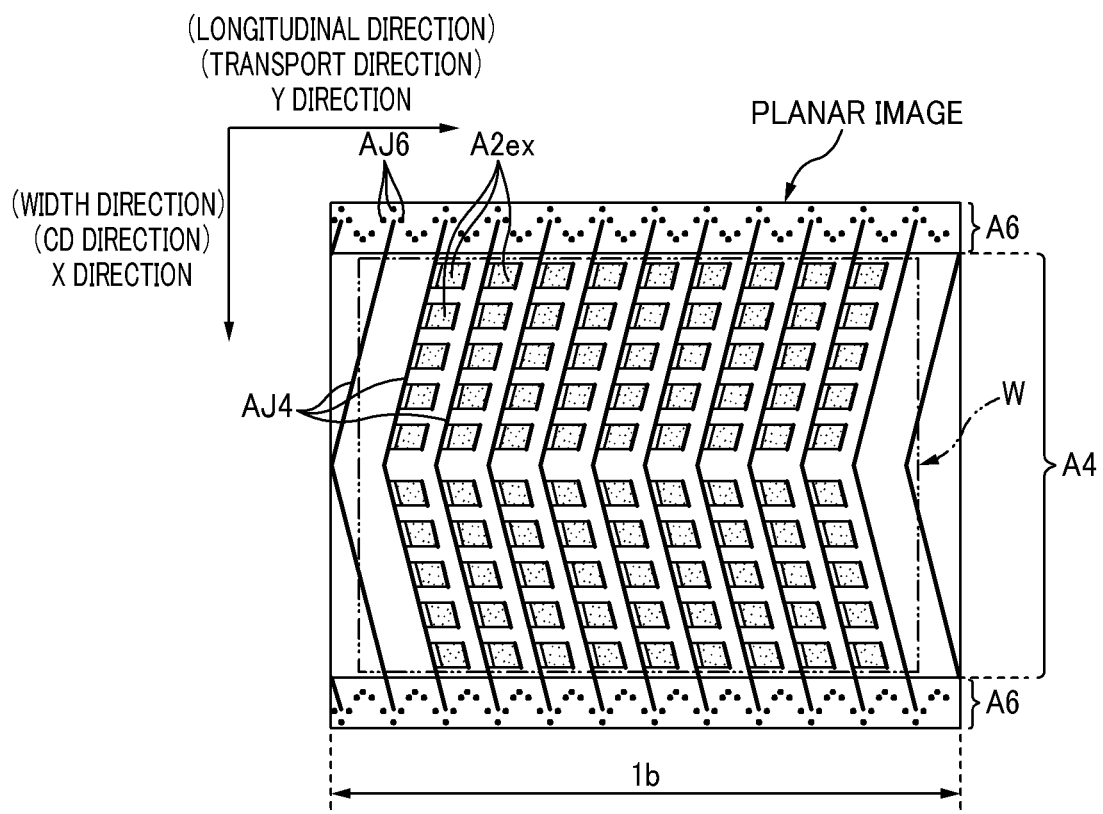
FIG. 7A is a planar image before passing through the binarization process.
Figure 7B:
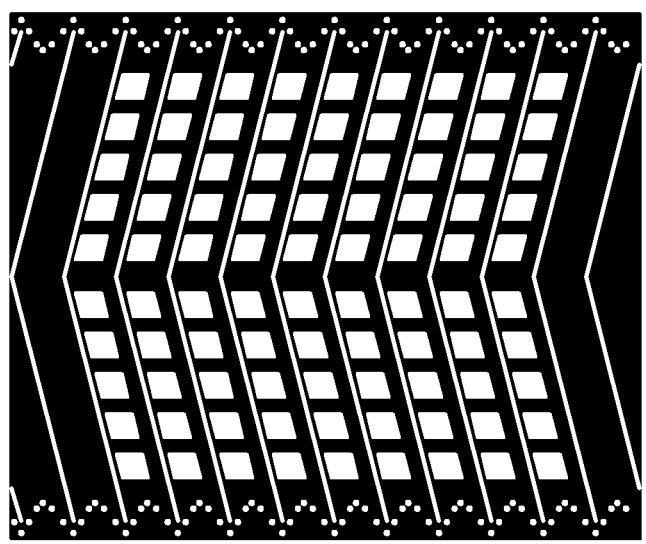
FIG. 7B is a binarized image created by performing the binarization process on the planar image.

FIGS. 7A and 7B are explanatory diagrams of the binarization process. FIG. 7A shows a planar image before passing through the binarization process and FIG. 7B is the binarized image generated by performing the binarization process on the planar image. In FIG. 7A, the area A2ex where the image of new exposed part 2ex in the planar image is captured, is shown in a dotted pattern.

First, before explaining the binarization process, description of the planar image and the planar image data will be given with reference to FIG. 7A.

An image of the planar image is, for example, captured with the CD direction as the X direction and the transport direction as the Y direction. Further, the image of the planar image has the entire area of the unit semi-manufactured product 1b captured as a single image.

This planar image is a collection of multiple picture elements respectively arranged in a grid form in both the X and Y directions at a predetermined pitch based on a predetermined resolution. That is, the planar image is configured of a line of picture elements composed of a plurality of picture elements aligned at a predetermined pitch in the X direction, that are arranged in a plurality of rows at a predetermined pitch in the Y direction. And the planar image data includes color information corresponding to each picture element. For example, when the planar image data is of a gray scale, each picture element has only brightness as the color information. And in such case, each picture element corresponding to high translucency areas in the unit semi-manufactured product 1b becomes bright so that the brightnesses of the picture elements take large values whereas the picture elements corresponding to low translucency areas in the unit semi-manufactured product 1b becomes dark so that the brightnesses of the picture elements take small values.

Here, the new exposed part 2ex created by the fiber raisable part 4kk in the unit semi-manufactured product 1b coming off, is in a state having almost all the long fibers of the long fibrous member 4 removed with substantially just the base material sheet 2 remaining (see FIGS. 4 and 2A), and this part 2ex is in a high translucency state in the thickness direction. Therefore, as will be described later, the picture element of the area A2ex in which the image of the new exposed part 2ex is captured, can be specified in the planar image shown in FIG. 7A by observing the picture elements having a brightness of a predetermined value or greater. Note that in the following, description is given assuming that the planar image data is gray scale data.

In the binarization process, predetermined binarization threshold values are used. And picture elements having brightness of this binarization threshold value or greater are assigned to white whereas picture elements having brightness smaller than this binarization threshold value are assigned to black. This is performed on all the picture elements in the planar image data and thereby, the area A2ex in which the image of the new exposed part 2ex is captured of the planar image shown in FIG. 7A, will be included in the white image specified by "1" of the two values as shown in FIG. 7B.

However, as can be seen from FIG. 7B, this white image includes captured image part AJ4 of the V-form joining line J4, captured image part AJ6 of the dotted adhering parts J6 in waveform arrangements created to the side sheet 6 and the like, besides the area A2ex in which the image of the new exposed part 2ex is captured. The reason for this is that the joining line J4 and the adhering part J6 have high translucency due to thinning by compression during the adhering process. Therefore, this white image includes such as the above described error, however, the effects of this error is eliminated in the following quality judgment process. This will be described later.

Next, the image processing part 66 proceeds to the quality judgment process. And in this quality judgment process, the area size of the white image in the binarized image shown in FIG. 7B is obtained first. The measurements of the planar size of the picture element here are known in advance based on each resolution and the like in the X and Y directions. Therefore, the area size of the white image is calculated by multiplying the number of picture elements being the number of picture elements assigned to the white image by the planar size of this picture element.

Then the image processing part 66 compares the area size of the calculated white image to the quality judgment threshold value stored in advance in the memory. And when the area of the white image is equal to or greater than the quality judgment value, the image processing part 66 judges that "there is enough number of the new exposed parts 2ex and thus the unit semi-manufactured product 1b as a whole is fiber raised normally". On the other hand, when the area of the white image is less than the quality judgment value, the image processing part 66 judges that "the number of the new exposed parts 2ex is small and thus the unit semi-manufactured product 1b as a whole is not fiber raised normally" and sets off an unsatisfactorily raised fiber alarm to the alarm output part 68 of the monitor and the like to notify the worker of the manufacturing line 10.

Here, this quality judgment threshold value is a fixed value stored in the memory in advance. And this quality judgment threshold value is obtained by an experimental method on the manufacturing line 10, as in the following. First, a number of samples of the web product 1 in a normal raised fiber state are prepared. Next, images of these samples are captured with the above described CCD camera 62 of the inspection device 60 to perform a binarization process for each sample and thereafter the area of the white image of each sample is obtained. Then the average value and the standard deviation u of the area of the white images for all the samples are calculated and the value smaller than this average value by 3$a$ is used as the aforementioned quality judgment threshold value.

Note that, according to such calculation method, the effects by the errors in the white image due to the aforementioned joining line J4 and the adhering part J6 can be substantially eliminated. To be specific, the area of the white image of each sample used for calculating this quality judgment threshold value also includes the captured image part AJ4 of the V-form joining line J4, the captured image part AJ6 of the dotted adhering parts J6 in waveform arrangement on the side sheet 6 and the like besides the area A2ex in which the image of the new exposed part 2ex is captured and therefore the areas of the white images take values excessive by the above amount. Therefore, when the quality judgment value calculated in this way is used, the error of the white image according to the binarized image of the aforementioned unit semi-manufactured product 1b is setoff with the aforementioned error included in the quality judgment threshold value, and an appropriate judgment can be made thereby. By the way, the quality judgment threshold value can be changed to a smaller value when judgment as being unsatisfactory is frequently made by the inspection device 60.

By the way, for some situations the target area to which the binarization process on the planar image of the unit semi-manufactured product 1b is performed can be limited to an area smaller than the planar image shown in FIG. 7A. For example, in the planar image of the unit semi-manufactured product 1b, only area A4 may be made the target of the binarization process, here area A4 is the area besides areas A6, A6 that have the images of both end parts in the width direction of the sides sheets 6, 6 of the unit semi-manufactured product 1b captured. And thereby, the effect by the aforementioned error due to the dotted adhering parts J6, J6 . . . in waveform arrangements formed to the side sheet 6 will be avoided, and as a result the accuracy of quality judgment of the raised fiber state can be improved. Description thereof will be given with reference to FIG. 7A in the following.

In this example, the image processing part 66 uses the inspection window W during the binarization process. This inspection window W is a tool that partitions and limits the area to be referred to in the planar image during the binarization process, in other words, only the picture elements that belong inside the inspection window W are referred to during the binarization process and those outside the inspection window W are not referred to. In this example, the inspection window W is set to be a rectangular frame of a planar size approximately the same as the area A4 in which the image of the long fibrous member 4 is captured. Therefore, of the planar image, only the area A4 with the areas A6, A6 that have the images of the sides sheets 6, 6 at both end parts in the width direction captured excluded, can be set as the target of the binarization process.

Note that such referring to the picture elements limited to those inside the inspection window W can be realized, for example, in the following manner. First, each picture element of the planar image is assigned X and Y coordinates and these X and Y coordinates are recorded in the memory. Further, the image processing part 66 is configured to be accessible to the color information of the picture elements belonging in the inspection window W by specifying these X and Y coordinates. Therefore, the aforementioned reference to the picture elements limited to those within the inspection window W can be realized when the data of the X and Y coordinates of the picture elements to be positioned in the inspection window W are recorded in the memory in advance.

By the way, in the above description, explanation of the long fibrous member 4 creation process S4 had not been given. So description of this creation process S4 will be given with reference to FIG. 5.

First, the tows 4$t$ being the material of the long fibrous member 4, are introduced to the manufacturing line 10. The tows 4$t$ being the long fibrous member 4 at the time of introduction have the bundles of fiber having, for example, a width of 10 to 60 mm folded in multiple layers in a fanfold state with regard to the longitudinal direction. Therefore, the tows 4$t$ are continuously fed to the transport path while having each of the multiple folded parts extended straight layer by layer.

Meanwhile, a fiber separating process S4$t$ is set to the transport path. And the tows 4$t$ are dispersed in the CD direction until the width dimension of the tows 4$t$ reach the width dimension of the long fibrous member 4 of the semi-manufactured product 1*a* while passing through this fiber separating process S4*t*. And then they are transported to the aforementioned joining point P4. Note that both sides of the base material sheet 2 each have the long fibrous members 4, 4 fed so that such creation process S4, S4 is provided for each of the top and bottom faces of the base material sheet 2.

Here, in the aforementioned fiber separating process S4*t*, there may be a situation where the basis weight is not uniformly distributed in the CD direction of the long fibrous member 4. And in such case, there will be parts whose basis weight of the long fibrous member 4 in the unit semi-manufactured product 1*b* is small, created locally. However, such parts with small basis weight having high translucency in the thickness direction will have their images captured as areas in the planar image with high brightness. Therefore, such parts are included in the white image same as the area A2*ex* in which the image of the new exposed part 2*ex* is captured during the aforementioned binarization process, thus being recognized as an error which may possibly lead to error judgment in the quality judgment on the raised fiber state.

For the purpose of avoiding such error judgment in the present embodiment, as shown in FIG. 5, a basis weight distribution inspection device 80 that inspects the distribution of the basis weight in the CD direction of the long fibrous member 4 is set at a location between the fiber separating process S4*t* and the joining point P4 to the transport path of the base material sheet 2 in the long fibrous member 4 transport path, for inspecting whether or not the basis weight distribution is made uniform to a degree that would not cause the aforementioned error.

As shown in FIG. 5, the basis weight distribution inspection devices 80, 80 are each provided to the long fibrous member 4 creation processes S4, S4. Further, the basic configuration of the basis weight distribution inspection devices 80, 80 are substantially the same as those in the aforementioned raised fiber state inspection device 60. In other words, the basis weight distribution inspection device 80 includes a CCD camera 82 as the third image capturing processing part, lighting member 84, and a third image capturing processing part 86 (corresponding to the third binarization processing part and the third quality judgment processing part). The camera 82 captures images by receiving the light of a transmitted beam transmitted through the long fibrous member 4 in the thickness direction. And this camera 82 captures an image of one side of the long fibrous member 4 at an appropriate image capturing timing based on a synchronization signal and the like, and creates the data of the planar image as the third planar image data. The third image capturing processing part 86 that receives the third planar image data performs binarization process for this third planar image data.

Here, areas in the long fibrous member 4 with small basis weight have high translucency and those with large basis weight have low translucency so that in the planar image, the brightness of the picture elements corresponding to the areas in the long fibrous member 4 with small basis weight is high and those corresponding to the areas in the long fibrous member 4 with large basis weight is low.

Figure 8A:
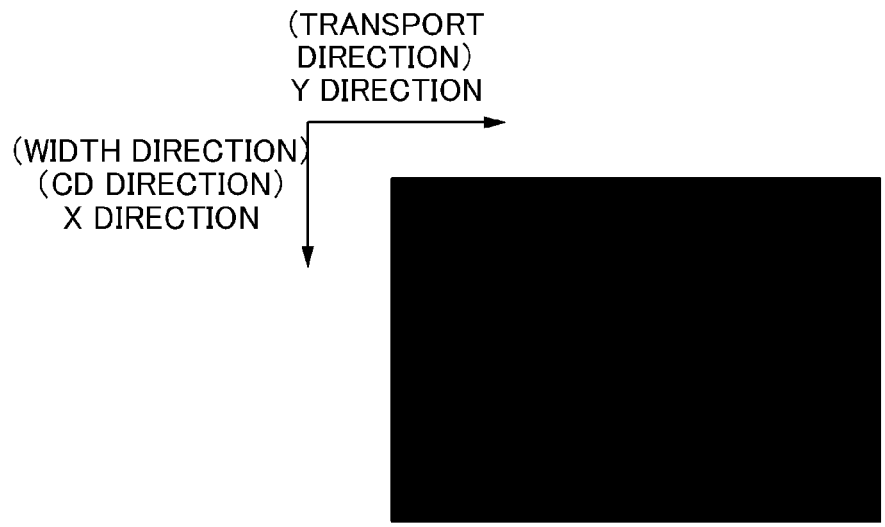
FIG. 8A is an example of a binarized image created by the basis weight distribution inspection device 80 where problems are not found with the basis weight distribution.

Meanwhile, in also this binarization process, a predetermined binarization threshold value is used. And picture elements with brightnesses equal to or larger than this binarization threshold value are allocated to white whereas picture elements with brightnesses less than this binarization threshold value are allocated to black. Therefore, when this binarization threshold value is set to, for example, a value equal to the brightness of the aforementioned part A2*ex* in which the image of the new exposed part 2*ex* in the planar image is captured, the area (corresponding to "an area in which an image of a part in the fibrous member having a basis weight equal to or smaller than a predetermined value is captured") in which the image of the part (corresponding to "a part in the fibrous member having a basis weight equal to or smaller than a predetermined value") with a small basis weight that may become the above mentioned error is captured, is included in the white image specified by "1" of the two values. On the other hand, when there is no such area, all the picture elements of the planar image are included in the black image and no white image exists in the binarized image, as shown in FIG. 8A.

Figure 8B:
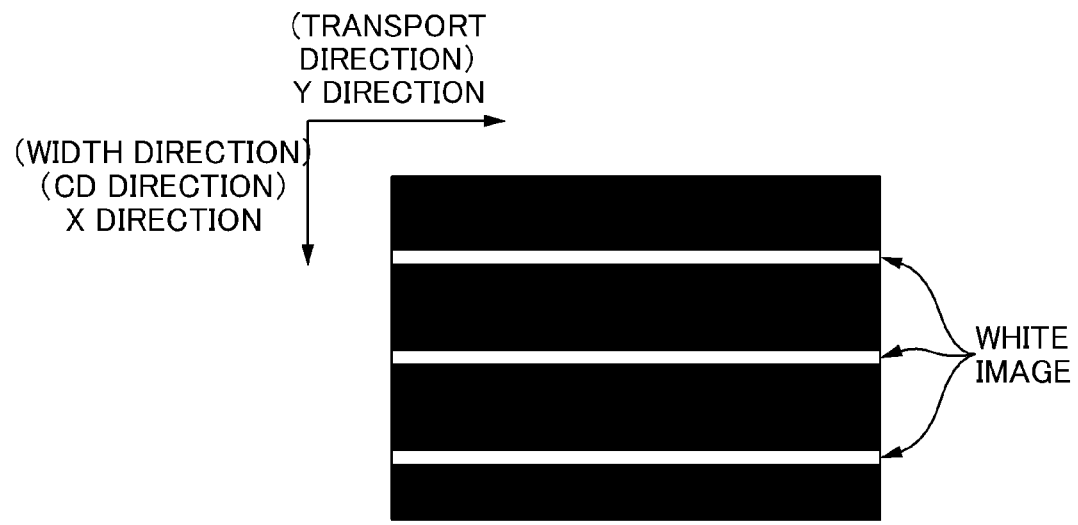
FIG. 8B is an example of a binarized image where problems are found with the basis weight distribution.

Thereafter, the third image capturing processing part 86 moves to the quality judgment process. Then the third image capturing processing part 86 checks, for example, whether or not there is a white image in the binarized image in the quality judgment process. And in the case where there is no white image as shown in FIG. 8A, the third image capturing processing part 86 judges that "the basis weight distribution is uniform to an extent that the above described error would not occur". On the other hand, in the case where there is a white image as shown in FIG. 8B, the third image capturing processing part 86 judges that "the basis weight distribution is not uniform to an extent that the above described error may be caused", and notifies to the worker of the manufacturing line 10 by sending an alarm indicating an abnormal basis weight distribution to the alarm output part 88 such as a monitor. Then the worker stops the manufacturing line 10 to perform an appropriate adjustment operation at the fiber separating process S4*t*, and hereby the basis weight distribution in the width direction of the long fibrous member 4 is made substantially uniform. And after such adjustment, the manufacturing line is resumed to restart manufacturing.

Note that in the aforementioned example, quality judgment was made by checking the existence of a white image in the binarized image, however the present invention is not limited to such. For example, quality judgment can be performed using the quality judgment threshold. In other words, a quality judgment threshold value stored in the memory in advance can be compared with the area of the white image shown in FIG. 8B, to judge that "the basis weight distribution is uniform to an extent that the above described error would not occur" when the area of the white image is smaller than the quality judgment threshold value whereas "the basis weight distribution is not uniform to an extent that the above described error may occur" when the area of the white image is equal to or greater than the quality judgment threshold value.

By the way, the target forming range C4M of the cutting line C4 formed in the raising fiber cutting process S40 had also not been explained in the aforementioned description. Therefore, description thereof will be given.

FIG. 9 is an enlarged planar view of the semi-manufactured product 1*a* shown with the target forming range C4M for the cutting line C4. As shown in FIG. 9, the cutting line C4 has the target forming range C4M formed to include the center position MJ4 between joining lines J4, J4 adjacent to each other in the transport direction, and the positions on the downstream side along the transport direction than this center position MJ4. The reason for this is as follows. As mentioned above, since the perforated cutting line C4 is formed in the V-form area R4 between the joining lines J4, J4 adjacent to each other in the transport direction, the long fibers in each area R4 are divided into two in the longitudinal direction, and the part 4*kk*1 positioned on the upstream side of these divided parts becomes the fiber raisable part 4*kk* and the part 4*kk*2 positioned on the downstream side becomes the unraised fiber part. Here, the dust scraping effect of the fiber raisable part 4kk when in a fibrous state depends on the height of the raised fiber of this fiber raisable part 4kk, that is, the higher the height of the raised fiber, the greater the scraping effect. Meanwhile, the height of the raised fiber depends on the length of the fiber raisable part 4kk in the longitudinal direction, that is, depends on the length in the transport direction, and this length takes substantially the same value as the distance D4kk in the transport direction between cutting line C4 and the joining line J4 positioned on the upstream side thereof. Therefore, for the purpose of securing a high fiber height, the target forming range C4M of the cutting line C4 is positioned to include the center position MJ4 between joining lines J4, J4 and the positions on the downstream side along the transport direction than the center position MJ4, as mentioned above.

However, there is a case where the position (corresponding to cutting position) where the actual cutting line C4 (corresponding to cutting trace) is formed is shifted from the above target forming range C4M in the transport direction due to synchronization failure and the like of the cutter rollers 40a, 40a of the raising fiber cutting process S40 to the sealing rollers 20a, 20b of the main sealing process S20. And for example, when this forming position is shifted from the target forming range C4M to the upstream side, the target fiber height cannot be secured and on the other hand when the forming position is shifted to the downstream side, the forming position would accord and the like with the joining line J4 positioned on the downstream side of the cutting line C4 so that in such case, there is a possibility that the fiber raisable part 4kk is not formed.

Thus for the purpose of solving such problem, the present embodiment has set between the raising fiber cutting process S40 and the fiber raising process S50, a cutting line inspection device 90 for inspecting the position where the cutting line C4 is formed, as shown in FIG. 5. Note that, the reason for positioning this inspection device 90 on the upstream side than the fiber raising process S50 is because it would be difficult to capture clear images of the cutting line C4 by such as the cutting line C4 being covered by the raised fiber if positioned after the fiber raising process S50.

As shown in FIG. 5, the basic configuration of the cutting line inspection device 90 is substantially the same as the aforementioned raised fiber state inspection device 60 and the basis weight distribution inspection device 80. In other words, the cutting line inspection device 90 includes a CCD camera 92 as the second image capturing processing part, a lighting member 94, and a second image processing part 96 (corresponding to the second binarization processing part and the second quality judgment processing part). The camera 92 captures images by receiving the light of a transmitted beam transmitted through the unit semi-manufactured product 1b in the thickness direction. And this camera 92 captures an image of one side of the unit semi-manufactured product 1b, for each unit semi-manufactured product 1b, at an image capturing timing similar to the aforementioned raised fiber state inspection device 60, that is, at a timing when the planar center of the unit semi-manufactured product 1b substantially matches the planar center of the planar image, and creates the data of the planar image as the second planar image data. The second image capturing processing part 96 that had received this second planar image data performs a binarization process to this second planar image data using the inspection window W1.

Figure 10:
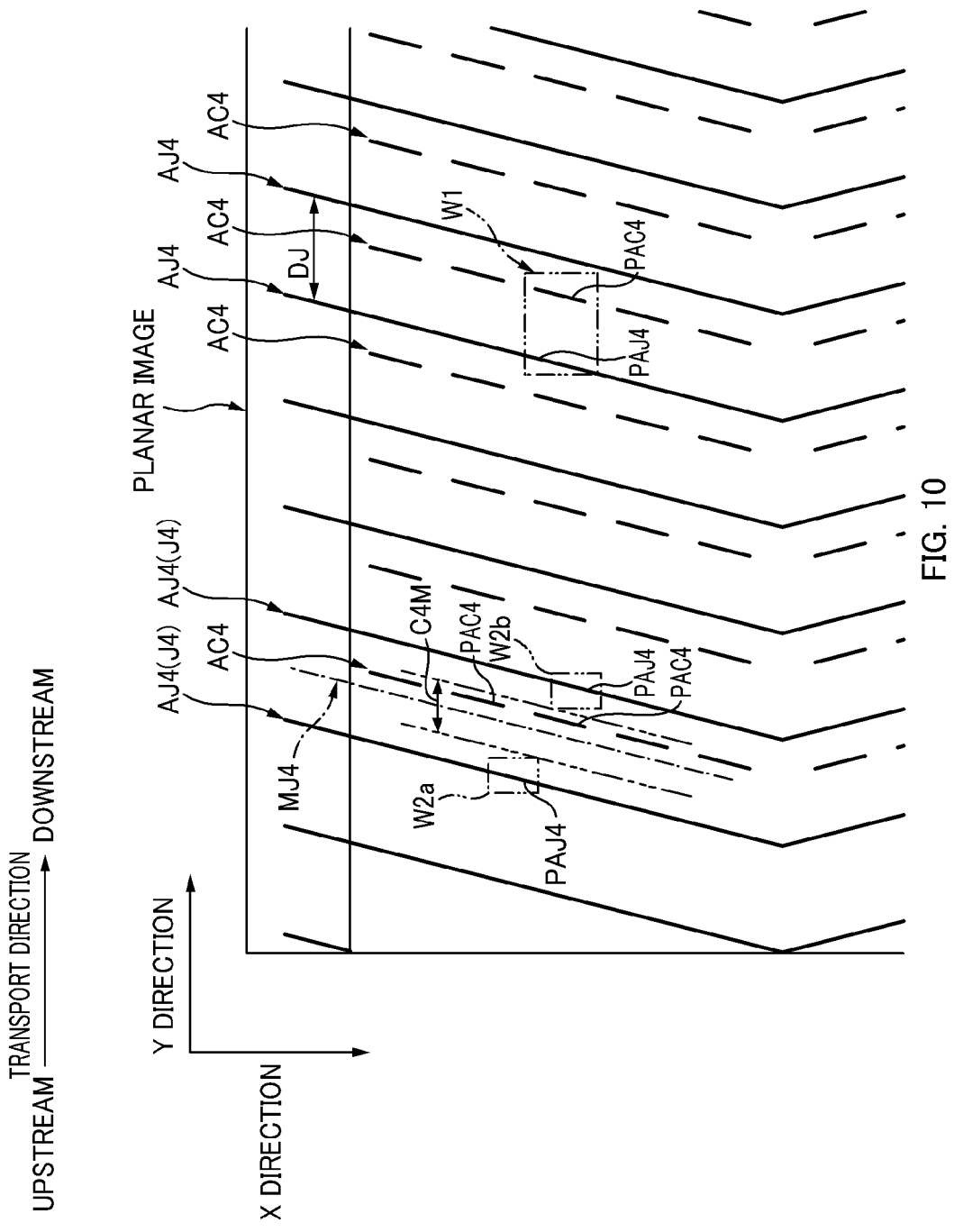
FIG. 10 is an enlarged view of the planar image for explaining the inspection windows W1, W2a, W2b set by the cutting line inspection device 90.
Figure 11:
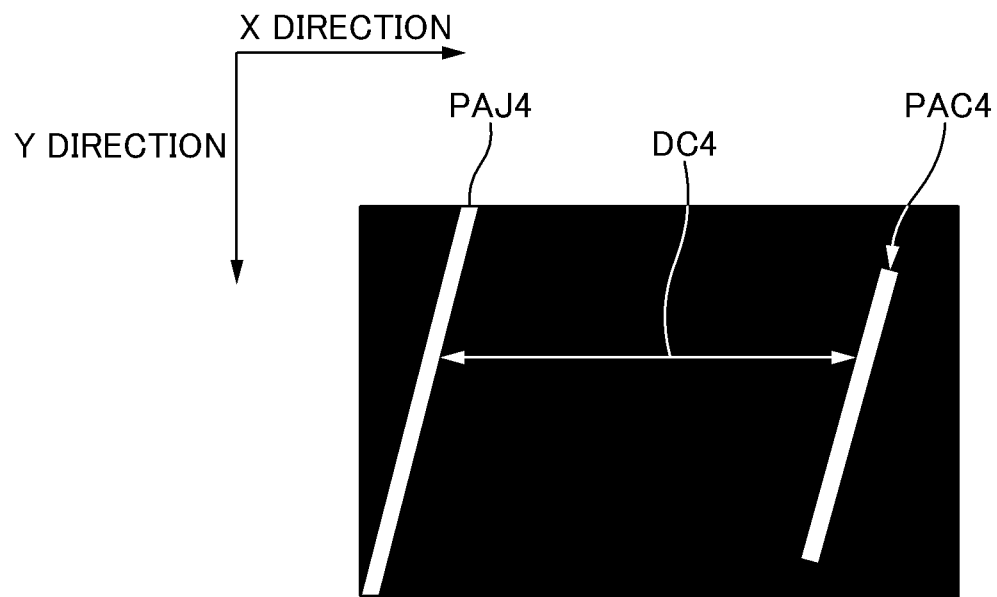
FIG. 11 is a view showing an example of a binarized image created based on the inspection window W1.

The inspection window W1 is shown together in the enlarged view of the planar image shown in FIG. 10. The inspection window W1 is set to a planar size so to include each one of a part PAC4 of the captured image part AC4 of the cutting line C4, and a part PAJ4 of the captured image part AJ4 of the joining line J4 upstream the part PAC4. Therefore a binarized image including in the white image a part PAC4 of the captured image part AC4 of the cutting line C4 and a part PAJ4 of the captured image part AJ4 of the joining line J4 is created, as shown in FIG. 11. In other words, since the cutting line C4 is formed in a porous condition by being perforated in the thickness direction of the unit semi-manufactured product 1b, the translucency of the cutting line C4 is high and the brightness of the picture element corresponding to the cutting line C4 is higher than the brightness of the picture element corresponding to the joining line J4, in the planar image. Therefore, the white image of the binarized image created based on a predetermined binarization threshold value, has included therein both a part PAJ4 (corresponding to the area where an image of a cutting trace is captured) of the captured image part AJ4 of the joining line J4 and a part PAC4 of the image capturing part AC4 of the cutting line C4, that are in the inspection window W1.

Then the process proceeds to the quality judgment process. In the quality judgment process, judgment is made on whether or not the cutting position of the cutting line C4 is positioned in the target forming range C4M, based on the value of the distance DC4 in the transport direction between the part PAC4 corresponding to the cutting line C4 in the white image and the part PAJ4 corresponding to the joining line J4 in the white image.

Therefore, at first, the second image capturing processing part 96 calculates the value of this distance DC4. This value of the distance DC4 can be obtained as the difference by, for example, subtracting the average value of the Y coordinates of the picture elements composing the part PAJ4 corresponding to the joining line J4 from the average value of the Y coordinates of the plurality of picture elements composing the part PAC4 corresponding to the cutting line C4. Note that, the differentiation between the picture elements composing the part PAC4 corresponding to the cutting line C4 and the picture elements composing the part PAJ4 corresponding to the joining line J4 can be made since, for example, each ranges of the X and Y coordinates in which the picture elements of the part PAJ4 corresponding to the joining line J4 exist is known in advance, so that the picture elements within this range are considered as the picture elements of the part PAJ4 corresponding to the joining line J4, and can be discriminated from others that are picture elements of the part PACO corresponding to the cutting line C4.

Then the value of the calculated distance DC4 is compared with the quality judgment threshold value. The quality judgment threshold value is stored in the memory in advance as a numerical value range. The lower limit of the numerical value range of the quality judgment threshold value is, for example, half the value of the distance DJ between the image capturing parts AJ4, AJ4 of the joining lines J4, J4 adjacent to each other, and the upper limit is a value slightly smaller than the distance DJ such as 0.9 times the above distance DJ (see FIG. 10).

And when the value of the above distance DC4 obtained is in the numerical value range, a judgment "the cutting line C4 is positioned within the target forming range C4M" is made, and on the other hand when the above distance DC4 is outside the numerical value range, a judgment "the cutting line C4 is positioned outside the target forming range C4M" is made.

By the way, when the judgment result is of the latter case, the second image capturing processing part 96 sends an instruction signal to correction the phase of the rotation angle value of the rotational movement to the servo motor amplifier of the cutter rollers 40a, 40b in the raising fiber cutting process S40. Then the amplifier that has received the above signal changes the phase of the rotation angle of the rotational movement of the cutter rollers 40a, 40b so that the value of the distance DC4 comes in the above numerical range.

Note that, as another example of the binarization process and the quality judgment process to be performed by the second image capturing processing part 96, for example, the following can be given.

First, as shown in FIG. 10, a pair of rectangular shape inspection windows W2a, W2b of the same planar size is provided to two places in the transport direction. Here, one of the inspection windows W2a is set so that the planar center of this inspection window W2a coincides with the captured image part AJ4 of the joining line J4 positioned upstream of the target forming range C4M of the cutting line C4, and the other inspection window W2b is set so that the planar center of this inspection window W2b coincides with the captured image part AJ4 of the joining line J4 positioned downstream of the target forming range C4M of the cutting line C4. Additionally, the planar sizes of the inspection windows W2a, W2b are set so that the target forming area C4M of the cutting line C4 does not enter into both of these inspection windows W2a, W2b.

Therefore, when the position where the actual cutting line C4 is formed is within the target forming range C4M, the captured image part AC4 of the cutting line C4 would not be included in both of the two inspection windows W2a, W2b so that the white image in the two binarized images at that time would be in a state including only the part PAJ4 of the captured image part AJ4 of the joining line J4, and none of the captured image part AC4 of the cutting line C4. On the other hand, when the position where the actual cutting line C4 is formed is outside the target forming range C4M in the transport direction, the captured image part AC4 of the cutting line C4 will be included in one of the two inspection windows W2a, W2b so that a part PACO of the captured image part AC4 of the cutting line C4 at that time would be included in one of the white images of the two binarized images. Therefore, in the quality judgment process performed hereafter, the quality judgment on the position where the cutting line C4 is formed will be performed by paying attention to the changes in the area of this white image.

In other words, in the quality judgment process on the position where the cutting line C4 is formed, each of the areas of the two white images of the binarized images are calculated first. Then the sizes of the areas are compared with the quality judgment threshold value set in advance, and when either of the areas is larger than the quality judgment threshold value, a judgment that "the position where the cutting line C4 is formed is outside the target forming range C4M" is made and in cases besides this, a judgment that "the position where the cutting line C4 is formed is within the target forming range C4M" is made. However, as can be seen from FIG. 10, this process example is a method that holds when the target forming range C4M is a predetermined range with the middle position MJ4 between the joining lines J4, J4 set as the center and as mentioned above, this is a method that cannot be applied when the target forming range C4M is shifted downstream in the transport direction as described above, and thus the aforementioned method is preferable.

Other Embodiments

While the present invention has been described in conjunction with the embodiments, it should be understood that the above embodiments have been presented for facilitating the understanding of the invention and not for construing the invention in a limited way. It should also be understood that the invention can be changed and modified without departing from the spirit of the invention, and naturally includes equivalents thereof. For example, variations as described below can be made.

Although grayscale data with color information of the picture elements including only the brightness was shown as an example of the planar image data in the aforementioned embodiment, the present invention is not limited to such. For example, the color information of the picture elements may be color image data including brightness, hue, and intensity. And in such case, color binarization process can be performed as the aforementioned binarization process.

By the way, a color binarization process is a process of extracting picture elements including specific color information from color image data of the planar image. Here, color information has numerical values for each of the three elements being brightness, hue, and intensity as mentioned above. Therefore, when the numerical value range of color information of the picture elements to be extracted are set in advance in the memory of the image processing parts 66, 86, 96 as binarization threshold values for each of the brightness, hue, and intensity, each of the image processing parts 66, 86, 96 can extract the set color information of the picture elements from the planar image.

In other words, if the aforementioned three numerical value ranges of the binarization threshold values are set in advance based on a color unique to the area A2ex in which the image of the new exposed part 2ex in the planar image is captured, the image processing parts 66, 86, 96 refers to the color information of the picture elements of the planar image recorded in the planar image data, and allocates picture elements satisfying all three numerical value ranges of the aforementioned binarization threshold values to, for example, white picture elements, and allocates the picture elements not satisfying the above to, for example, black picture elements. And this allocating operation is performed for all the picture elements in the planar image data, and thereby the area A2ex in which the image of the new exposed part 2ex in the planar image is captured, is extracted as the area of the white picture elements. According to this method, the above area A2ex in which the image of the new exposed part 2ex in the planar image is captured is extracted from the planar image based on the color unique to this area so that the accuracy of extraction can be improved. Note that the contents besides those mentioned above are the same as those already mentioned giving grayscale as an example, therefore explanation thereof is omitted.

Although the image processing parts 66, 86, 96 had made quality judgments based on the area of the white image in the binarized image in the aforementioned embodiment, the present invention is not limited to such. In other words, values besides those indicating area can be used as long as the values indicate the sizes of the white image. For example, quality judgment can be made using the number of the picture elements in the white image. And in such case, fixed values expressed by the amount of the picture elements are each set in the memories of the image processing parts 66, 86, 96 in advance as the quality judgment threshold values.

Although the semi-manufactured product 1a having long fibrous members 4, 4 layered on each of the two sides of the base material sheet 2 has been shown as an example of the web member in the aforementioned embodiment, the present invention is not limited to such and for example, such having along fibrous member 4 layered on only one side of the base material sheet 2 may be set as the web member. In other words, the other side need not be layered.

Although the raised fiber state inspection device 60 and the cutting line inspection device 90 had been set separately in the aforementioned embodiment, there may be a case where the raised fiber state inspection device 60 is configured to serve also as the cutting line inspection device 90, and the cutting line inspection device 90 may be omitted.

In the aforementioned embodiment, the cutting line C4 formed along the joining line J4 were formed in a V form since the planar form of the joining line J4 were in a V form. And as a result, each of the fiber raisable parts 4kk, 4kk . . . were also arranged in V form, however, the arrangement pattern of these fiber raisable parts 4kk, 4kk . . . is not limited to such. In other words, the arrangement pattern may be besides that above as long as the arrangement pattern of the plurality of the fiber raisable parts 4kk, 4kk . . . are in a dispersed arrangement. For example, a staggered arrangement or a lattice arrangement will do.

REFERENCE SIGNS LIST 1 web product, 1a semi-manufactured product (web member), 1b unit semi-manufactured product, 2 base material sheet (continuous web), 2ex new exposed part, 2n band shaped part, 4 long fibrous member (fibrous member), 4J joining line (joining part), 4f end part, 4k brush part, 4kk fiber raisable part (fiber raisable part), 4kk1 fiber raisable part, 4kk2 non-raised fiber part, 4c fiber raisable part, 4n non-cut part (not yet cut part), 4se cut end part, 4t tow, 6 side sheet, 10 manufacturing line, 12 reel device, 20a upper sealing roller, 20b lower sealing roller, 30a upper sealing roller, 30b lower sealing roller, 40a upper cutter roller, 40b lower cutter roller, 50a upper brush roller, 50b lower brush roller, 60 raised fiber state inspection device (inspection device), 62 CCD camera (image capturing processing part), 64 lighting member, 66 image processing part (binarization processing part, quality judgment processing part), 68 alarm output part, 70a upper cutter roller, 70b lower cutter roller, 80 basis weight distribution inspection device, 82 CCD camera (third image capturing processing part), 84 lighting member, 86 third image processing part (third binarization processing part, third quality judgment processing part), 88 alarm output part, 90 cutting line inspection device, 92 CCD camera (second image capturing processing part), 94 lighting member, 96 second image processing part (second binarization processing part, second quality judgment processing part), S4 long fibrous member creation process, S4t fiber separating process, S20 main sealing process, S30 side sealing process, S40 raising fiber cutting process, S50 fiber raising process, S60 raised fiber state inspection process, S70 end cutting process, P4 joining point, P6 joining point, PS image capturing position, A2ex image capturing part (area in which an image of a new exposed part is captured), A4 area, A6 area, R4 area, C4 cutting line, C4M target forming range, J4 joining line, J6 adhering part, W inspection window, W1 inspection window, W2a inspection window, W2b inspection window, AC4 captured image part of the cutting line, PACO part (corresponding part, area where an image of a cutting trace is captured), AJ4 captured image part of the joining line, PAJ4 part (corresponding part), AJ6 captured image part of the dotted adhering parts, and MJ4 center position.

The invention claimed is:

1. A device for inspecting a raised fiber state of a web member of a sanitary article, the web member having, on at least one face, fiber raisable parts that come off from the one face in a predetermined dispersed arrangement pattern, new exposed parts being created on the one face when the fiber raisable parts come off to be raised, wherein
the inspection device includes:
an image capturing processing part that captures an image of the one face and creates as a planar image data, a data of a planar image of the one face;
a binarization processing part that performs, when creating a binarized image based on the planar image data, a binarization process so that areas in which images of the new exposed parts in the planar image are captured, are included in an image specified by one value of two values in the binarized image; and
a quality judgment processing part that performs quality judgment of the raised fiber state based on an image specified by one value of two values,
the web member includes a continuous web continuing along a transport direction and a fibrous member provided to cover at least one face of the continuous web,
the fibrous member has a fiber direction positioned along the transport direction,
joining parts that join the continuous web and the fibrous member, are formed intermittently in the transport direction, and
the fiber raisable parts are formed by cutting the fibrous member at a cutting position between the joining parts adjacent to each other in the transport direction and configuring a cut end part of the fibrous member to be standable with the joining part as a base end part,
the device for inspecting the raised fiber state of the web member of the sanitary article further including
a second image capturing processing part that captures an image of a face of the fibrous member side of the web member and creates a planar image data of the fibrous member as a second planar image data,
a second binarization processing part that performs, when creating a binarized image based on the second planar image data, a binarization process so that an area is included in an image specified by one value of two values in the binarized image, an image of a cutting trace made by cutting at the cutting position being captured in the area, and
a second quality judgment processing part that judges whether or not the cutting position is positioned in a target forming range with regard to the transport direction, based on the second planar image data and based on an image specified by one value of two values.

2. A device for inspecting a raised fiber state of a web member of a sanitary article according to claim 1, wherein
the second image capturing processing part captures an image of a face on the fibrous member side of the web member, before the fiber raisable parts of the fibrous member come to be in the raised fiber state, and creates the second planar image data.

3. A device for inspecting a raised fiber state of a web member of a sanitary article, the web member having, on at least one face, fiber raisable parts that come off from the one face in a predetermined dispersed arrangement pattern, new exposed parts being created on the one face when the fiber raisable parts come off to be raised, wherein
the inspection device includes:
an image capturing processing part that captures an image of the one face and creates as a planar image data, a data of a planar image of the one face;
a binarization processing part that performs, when creating a binarized image based on the planar image data, a binarization process so that areas in which images of the new exposed parts in the planar image are captured, are included in an image specified by one value of two values in the binarized image; and a quality judgment processing part that performs quality judgment of the raised fiber state based on an image specified by one value of two values, the web member includes a continuous web continuing along a transport direction and a fibrous member provided to cover at least one face of the continuous web, the fibrous member is transported in the transport direction integral with the continuous web in a state covering the one face of the continuous web by being layered on the one face of the continuous web at a predetermined position in the transport direction of the continuous web, the fibrous member has a width direction in a direction orthogonal to the transport direction, the device for inspecting the raised fiber state of the web member of the sanitary article further including a third image capturing processing part that captures from one face side an image of the fibrous member before being layered on the continuous web, and creates a planar image data of the fibrous member as a third planar image data, a third binarization processing part that performs, when creating a binarized image based on the third planar image data, a binarization process so that an area is included in an image specified by one value of two values in the binarized image, an image of a part in the fibrous member having a basis weight equal to or smaller than a predetermined value being captured in the area, and a third quality judgment processing part that judges whether or not the basis weight of the fibrous member is uniform in the width direction, based on the third planar image data and based on an image specified by one value of two values.

4. A device for inspecting a raised fiber state of a web member of a sanitary article according to claim 1, wherein the web member is a continuous body continuing in the transport direction, both end parts, of the one side of the web member, in the width direction orthogonal to the transport direction do not have the fiber raisable parts provided and the both end parts have thinned adhering parts formed, and the binarization processing part creates the binarized image with an area besides the area in which an image of the both ends among the planar image is captured as a target of the binarization process.

5. A method for inspecting a raised fiber state of a web member of a sanitary article, the web member having, on at least one face, fiber raisable parts that come off from the one face in a predetermined dispersed arrangement pattern, new exposed parts being created on the one face when the fiber raisable parts come off to be raised, wherein the inspection method includes:

capturing an image of the one face and creating as a planar image data, a data of a planar image of the one face;

performing, when creating a binarized image based on the planar image data, a binarization process so that areas in which images of the new exposed parts in the planar image are captured, are included in an image specified by one value of two values in the binarized image; and performing quality judgment of the raised fiber state based on a value indicating a size of the image specified by one value of two values in the binarized image the web member including a continuous web continuing along a transport direction and a fibrous member provided to cover at least one face of the continuous web, the fibrous member having a fiber direction positioned along the transport direction, joining parts that join the continuous web and the fibrous member, being formed intermittently in the transport direction, and the fiber raisable parts being formed by cutting the fibrous member at a cutting position between the joining parts adjacent to each other in the transport direction and configuring a cut end part of the fibrous member to be standable with the joining part as a base end part, the method for inspecting the raised fiber state of the web member of the sanitary article further including capturing an image of a face of the fibrous member side of the web member and creating a planar image data of the fibrous member as a second planar image data, performing, when creating a binarized image based on the second planar image data, a binarization process so that an area is included in an image specified by one value of two values in the binarized image, an image of a cutting trace made by cutting at the cutting position being captured in the area, and judging whether or not the cutting position is positioned in a target forming range with regard to the transport direction, based on the second planar image data and based on an image specified by one value of two values.

6. A method for inspecting a raised fiber state of a web member of a sanitary article, the web member having, on at least one face, fiber raisable parts that come off from the one face in a predetermined dispersed arrangement pattern, new exposed parts being created on the one face when the fiber raisable parts come off to be raised, wherein the inspection method includes:

capturing an image of the one face and creating as a planar image data, a data of a planar image of the one face;

performing, when creating a binarized image based on the planar image data, a binarization process so that areas in which images of the new exposed parts in the planar image are captured, are included in an image specified by one value of two values in the binarized image; and performing quality judgment of the raised fiber state based on a value indicating a size of the image specified by one value of two values in the binarized image; and the web member including a continuous web continuing along a transport direction and a fibrous member provided to cover at least one face of the continuous web, the fibrous member being transported in the transport direction integral with the continuous web in a state covering the one face of the continuous web by being layered on the one face of the continuous web at a predetermined position in the transport direction of the continuous web, the fibrous member having a width direction in a direction orthogonal to the transport direction, the method for inspecting the raised fiber state of the web member of the sanitary article further capturing from one face side an image of the fibrous member before being layered on the continuous web, and creating a planar image data of the fibrous member as a third planar image data, performing, when creating a binarized image based on the third planar image data, a binarization process so that an area is included in an image specified by one value of two values in the binarized image, an image of a part in the fibrous member having a basis weight equal to or smaller than a predetermined value being captured in the area, and judging whether or not the basis weight of the fibrous member is uniform in the width direction, based on the third planar image data and based on an image specified by one value of two values.

7. A device for inspecting a raised fiber state of a web member of a sanitary article according to claim 2, wherein the web member is a continuous body continuing in the transport direction, both end parts, of the one side of the web member, in the width direction orthogonal to the transport direction do not have the fiber raisable parts provided and the both end parts have thinned adhering parts formed, and the binarization processing part creates the binarized image with an area besides the area in which an image of the both ends among the planar image is captured as a target of the binarization process.

8. A device for inspecting a raised fiber state of a web member of a sanitary article according to claim 3, wherein the web member is a continuous body continuing in the transport direction, both end parts, of the one side of the web member, in the width direction orthogonal to the transport direction do not have the fiber raisable parts provided and the both end parts have thinned adhering parts formed, and the binarization processing part creates the binarized image with an area besides the area in which an image of the both ends among the planar image is captured as a target of the binarization process.

* * * * *